(12) United States Patent
Liu et al.

(10) Patent No.: US 8,394,997 B2
(45) Date of Patent: Mar. 12, 2013

(54) PROCESS FOR THE ISOMERIZATION OF 2,2,4,4-TETRAALKYLCYCLOBUTANE-1,3-DIOLS

(75) Inventors: Zhufang Liu, Kingsport, TN (US); Lori Cooke Ensor, Blountville, TN (US); Kelmara Khadene Kelly, Longview, TX (US); Jerome Leonard Stavinoha, Jr., Longview, TX (US); Kim Steven Chamberlin, Kingsport, TN (US); Charles Everette Kelly, Kingsport, TN (US); Carey Dan Ashcroft, Longview, TX (US); Charles Edwan Sumner, Jr., Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 190 days.

(21) Appl. No.: 12/963,703

(22) Filed: Dec. 9, 2010

(65) Prior Publication Data

US 2012/0149948 A1    Jun. 14, 2012

(51) Int. Cl.
*C07C 35/04* (2006.01)
*C07C 29/145* (2006.01)

(52) U.S. Cl. ................................................... 568/839
(58) Field of Classification Search .................. 568/839
See application file for complete search history.

(56) References Cited

U.S. PATENT DOCUMENTS

| | | | |
|---|---|---|---|
| 1,602,699 A | 10/1926 | Nightingale | |
| 2,160,841 A | 6/1939 | Dreyfus | |
| 2,202,046 A | 5/1940 | Dreyfus et al. | |
| 2,278,537 A | 4/1942 | Dreyfus et al. | |
| 2,720,507 A | 10/1955 | Caldwell | |
| 2,806,064 A | 9/1957 | McKlveen | |
| 2,901,466 A | 8/1959 | Kibler | |
| 2,936,324 A | 5/1960 | Hasek et al. | |
| 3,000,906 A | 9/1961 | Hasek et al. | |
| 3,030,335 A | 4/1962 | Goldberg | |
| 3,062,852 A | 11/1962 | Martin et al. | |
| 3,075,952 A | 1/1963 | Coover et al. | |
| 3,091,600 A | 5/1963 | Caldwell et al. | |
| 3,169,121 A | 2/1965 | Goldberg et al. | |
| 3,190,928 A | 6/1965 | Elam et al. | |
| 3,201,474 A | 8/1965 | Hasek et al. | |
| 3,207,814 A | 9/1965 | Goldberg et al. | |
| 3,218,372 A | 11/1965 | Okamura et al. | |
| 3,227,764 A | 1/1966 | Martin et al. | |
| 3,236,899 A | 2/1966 | Clark | |
| 3,249,652 A | 5/1966 | Quisenberry | |
| 3,259,469 A | 7/1966 | Painter et al. | |
| 3,287,390 A | 11/1966 | Poos et al. | |
| 3,288,854 A | 11/1966 | Martin | |
| 3,312,741 A | 4/1967 | Martin | |
| 3,313,777 A | 4/1967 | Elam et al. | |
| 3,317,466 A | 5/1967 | Caldwell et al. | |
| 3,329,722 A | 7/1967 | Rylander | |
| 3,360,547 A | 12/1967 | Wilson et al. | |
| 3,366,689 A | 1/1968 | Maeda et al. | |
| 3,386,935 A | 6/1968 | Jackson et al. | |
| 3,403,181 A | 9/1968 | Painter et al. | |
| T858012 I4 | 1/1969 | Caldwell et al. | |
| 3,484,339 A | 12/1969 | Caldwell | |
| 3,502,620 A | 3/1970 | Caldwell | |
| T873016 I4 | 4/1970 | Gilkey et al. | |
| 3,541,059 A | 11/1970 | Schaper | |
| 3,546,177 A | 12/1970 | Kibler et al. | |
| 3,629,202 A | 12/1971 | Gilkey et al. | |
| RE27,682 E | 6/1973 | Schnell et al. | |
| 3,772,405 A | 11/1973 | Hamb | |
| 3,799,953 A | 3/1974 | Freitag et al. | |
| 3,907,754 A | 9/1975 | Tershansy et al. | |
| 3,915,913 A | 10/1975 | Jackson, Jr. et al. | |
| 3,962,189 A | 6/1976 | Russin et al. | |
| 4,001,184 A | 1/1977 | Scott | |
| 4,010,145 A | 3/1977 | Russin et al. | |
| 4,046,933 A | 9/1977 | Stefanik | |
| 4,056,504 A | 11/1977 | Grundmeier et al. | |
| 4,084,889 A | 4/1978 | Vischer, Jr. | |
| 4,125,572 A | 11/1978 | Scott | |
| 4,156,069 A | 5/1979 | Prevorsek et al. | |
| 4,160,383 A | 7/1979 | Rauschenberger | |
| 4,185,009 A | 1/1980 | Idel et al. | |
| 4,188,314 A | 2/1980 | Fox et al. | |
| 4,194,038 A | 3/1980 | Baker et al. | |
| 4,263,364 A | 4/1981 | Seymour et al. | |
| 4,356,299 A | 10/1982 | Cholod et al. | |

(Continued)

FOREIGN PATENT DOCUMENTS

| | | |
|---|---|---|
| BE | 615850 | 4/1962 |
| CA | 2035149 | 8/1991 |
| DE | 29 21 868 A1 | 12/1980 |
| DE | 197 27 709 | 6/1997 |
| DE | 198 11 773 A1 | 9/1999 |
| EP | 0 039 838 A1 | 11/1981 |
| EP | 0 273 144 | 5/1987 |
| EP | 0 282 277 | 9/1988 |
| EP | 0 372 846 | 6/1990 |
| EP | 0 544 008 A1 | 6/1993 |

(Continued)

OTHER PUBLICATIONS

Abstract of U.S. Defense Publication T869,015, 869 O.G. 714, Dec. 16, 1969.

(Continued)

*Primary Examiner* — Brian J Davis
(74) *Attorney, Agent, or Firm* — Jennifer R. Knight; Eric D. Middlemas

(57) ABSTRACT

Disclosed is a process for the isomerization of 2,2,4,4-tetraalkylcyclobutane-1,3-diols, such as 2,2,4,4-tetramethylcyclobutane-1,3-diol, by contacting the diol with a supported ruthenium catalyst in the presence of hydrogen at elevated pressures and temperatures. The process is carried under conditions in which there is no net production of 2,2,4,4-tetraalkylcyclobutane-1,3-diol. The process may be carried out in the presence or absence of a solvent and in the liquid or vapor phase.

18 Claims, 1 Drawing Sheet

U.S. PATENT DOCUMENTS

| | | | |
|---|---|---|---|
| 4,367,186 A | 1/1983 | Adelmann et al. |
| 4,379,802 A | 4/1983 | Weaver et al. |
| 4,384,106 A | 5/1983 | Go et al. |
| 4,391,954 A | 7/1983 | Scott |
| 4,424,140 A | 1/1984 | Weinberg et al. |
| 4,426,512 A | 1/1984 | Barbee et al. |
| 4,427,614 A | 1/1984 | Barham et al. |
| 4,430,484 A | 2/1984 | Quinn |
| 4,431,793 A | 2/1984 | Rosenquist |
| 4,452,933 A | 6/1984 | McCready |
| 4,465,820 A | 8/1984 | Miller et al. |
| 4,469,861 A | 9/1984 | Mark et al. |
| 4,480,086 A | 10/1984 | O'Neill |
| 4,525,504 A | 6/1985 | Morris et al. |
| 4,578,295 A | 3/1986 | Jabarin |
| 4,578,437 A | 3/1986 | Light et al. |
| 4,642,959 A | 2/1987 | Swiech, Jr. et al. |
| 4,738,880 A | 4/1988 | Asada et al. |
| 4,749,773 A | 6/1988 | Weaver et al. |
| 4,786,692 A | 11/1988 | Allen et al. |
| 4,816,308 A | 3/1989 | Shimizu et al. |
| 4,826,903 A | 5/1989 | Weaver et al. |
| 4,845,188 A | 7/1989 | Weaver et al. |
| 4,880,592 A | 11/1989 | Martini et al. |
| 4,882,412 A | 11/1989 | Weaver et al. |
| 4,892,922 A | 1/1990 | Weaver et al. |
| 4,892,923 A | 1/1990 | Weaver et al. |
| 4,937,134 A | 6/1990 | Schrenk et al. |
| 4,939,186 A | 7/1990 | Nelson et al. |
| 4,976,057 A | 12/1990 | Bianchi |
| 4,981,898 A | 1/1991 | Bassett |
| 4,985,342 A | 1/1991 | Muramoto et al. |
| 5,017,679 A | 5/1991 | Chang et al. |
| 5,017,680 A | 5/1991 | Sublett |
| 5,034,252 A | 7/1991 | Nilsson et al. |
| 5,104,450 A | 4/1992 | Sand et al. |
| 5,118,760 A | 6/1992 | Blakely et al. |
| 5,118,847 A | 6/1992 | Jackson et al. |
| 5,142,088 A | 8/1992 | Phelps et al. |
| 5,169,994 A | 12/1992 | Sumner, Jr. et al. |
| 5,183,863 A | 2/1993 | Nakamura et al. |
| 5,191,038 A | 3/1993 | Krabbenhoft et al. |
| 5,207,967 A | 5/1993 | Small et al. |
| 5,219,510 A | 6/1993 | Machell et al. |
| 5,224,958 A | 7/1993 | Warunek et al. |
| 5,239,020 A | 8/1993 | Morris |
| 5,256,761 A | 10/1993 | Blount, Jr. |
| 5,258,556 A | 11/1993 | Sumner, Jr. et al. |
| 5,268,219 A | 12/1993 | Harada et al. |
| 5,288,715 A | 2/1994 | Machell et al. |
| 5,288,764 A | 2/1994 | Rotter et al. |
| 5,292,783 A | 3/1994 | Buchanan et al. |
| 5,310,611 A | 5/1994 | Okabe et al. |
| 5,310,787 A | 5/1994 | Kutsuwa et al. |
| 5,326,584 A | 7/1994 | Kamel et al. |
| 5,326,821 A | 7/1994 | Sasaki et al. |
| 5,331,034 A | 7/1994 | Pfahler et al. |
| 5,333,073 A | 7/1994 | Suzuki |
| 5,354,791 A | 10/1994 | Gallucci |
| 5,372,864 A | 12/1994 | Weaver et al. |
| 5,372,879 A | 12/1994 | Handa et al. |
| 5,378,796 A | 1/1995 | George et al. |
| 5,382,292 A | 1/1995 | Conroy et al. |
| 5,384,377 A | 1/1995 | Weaver et al. |
| 5,475,144 A | 12/1995 | Watson et al. |
| 5,480,926 A | 1/1996 | Fagerburg et al. |
| 5,486,562 A | 1/1996 | Borman et al. |
| 5,489,665 A | 2/1996 | Yamato et al. |
| 5,494,992 A | 2/1996 | Kanno et al. |
| 5,498,668 A | 3/1996 | Scott |
| 5,498,688 A | 3/1996 | Oshino et al. |
| 5,506,014 A | 4/1996 | Minnick |
| 5,523,382 A | 6/1996 | Beavers et al. |
| 5,534,609 A | 7/1996 | Lewis et al. |
| 5,552,512 A | 9/1996 | Sublett |
| 5,591,530 A | 1/1997 | Warner et al. |
| 5,633,340 A | 5/1997 | Hoffman et al. |
| 5,650,453 A | 7/1997 | Eckberg et al. |
| 5,654,347 A | 8/1997 | Khemani et al. |
| 5,656,715 A | 8/1997 | Dickerson et al. |
| 5,668,243 A | 9/1997 | Yau et al. |
| 5,681,918 A | 10/1997 | Adams et al. |
| 5,688,874 A | 11/1997 | Hoffman |
| 5,696,176 A | 12/1997 | Khemani et al. |
| 5,705,575 A | 1/1998 | Kelsey |
| 5,783,307 A | 7/1998 | Fagerburg et al. |
| 5,804,617 A | 9/1998 | Hoffman et al. |
| 5,814,679 A | 9/1998 | Eckberg et al. |
| 5,859,116 A | 1/1999 | Shih |
| 5,863,622 A | 1/1999 | Jester |
| 5,902,631 A | 5/1999 | Wang et al. |
| 5,907,026 A | 5/1999 | Factor et al. |
| 5,942,585 A | 8/1999 | Scott et al. |
| 5,955,565 A | 9/1999 | Morris et al. |
| 5,958,539 A | 9/1999 | Eckart et al. |
| 5,958,581 A | 9/1999 | Khanarian et al. |
| 5,959,066 A | 9/1999 | Charbonneau et al. |
| 5,962,625 A | 10/1999 | Yau |
| 5,977,347 A | 11/1999 | Shuto et al. |
| 5,989,663 A | 11/1999 | Morris et al. |
| 6,001,910 A | 12/1999 | Blumenthal et al. |
| 6,005,059 A | 12/1999 | Scott et al. |
| 6,011,124 A | 1/2000 | Scott et al. |
| 6,012,597 A | 1/2000 | Nishihara et al. |
| 6,022,603 A | 2/2000 | Umeda et al. |
| 6,025,061 A | 2/2000 | Khanarian et al. |
| 6,030,671 A | 2/2000 | Yang et al. |
| 6,037,424 A | 3/2000 | Scott et al. |
| 6,043,322 A | 3/2000 | Scott et al. |
| 6,044,996 A | 4/2000 | Carew et al. |
| 6,063,464 A | 5/2000 | Charbonneau et al. |
| 6,063,465 A | 5/2000 | Charbonneau et al. |
| 6,063,495 A | 5/2000 | Charbonneau et al. |
| 6,084,019 A | 7/2000 | Matayabas et al. |
| 6,096,854 A | 8/2000 | Morris et al. |
| 6,114,575 A | 9/2000 | McMahon et al. |
| 6,120,477 A | 9/2000 | Campbell et al. |
| 6,120,889 A | 9/2000 | Turner et al. |
| 6,126,992 A | 10/2000 | Khanarian et al. |
| 6,127,492 A | 10/2000 | Nagashima et al. |
| 6,146,228 A | 11/2000 | Mougin et al. |
| 6,150,494 A | 11/2000 | Wang et al. |
| 6,183,848 B1 | 2/2001 | Turner et al. |
| 6,191,209 B1 | 2/2001 | Andrews et al. |
| 6,211,309 B1 | 4/2001 | McIntosh et al. |
| 6,221,556 B1 | 4/2001 | Gallucci et al. |
| 6,225,436 B1 | 5/2001 | Eiffler et al. |
| 6,232,504 B1 | 5/2001 | Barteau et al. |
| 6,239,210 B1 | 5/2001 | Kim et al. |
| 6,255,523 B1 | 7/2001 | Panandiker et al. |
| 6,287,656 B1 | 9/2001 | Turner et al. |
| 6,307,006 B1 | 10/2001 | Konig et al. |
| 6,309,718 B1 | 10/2001 | Sprayberry |
| 6,320,042 B1 | 11/2001 | Michihata et al. |
| 6,323,291 B1 | 11/2001 | Mason et al. |
| 6,323,304 B1 | 11/2001 | Lemmon et al. |
| 6,342,304 B1 | 1/2002 | Buchanan et al. |
| 6,352,783 B1 | 3/2002 | Fagerburg |
| 6,354,986 B1 | 3/2002 | Hlavinka et al. |
| 6,359,070 B1 | 3/2002 | Khanarian et al. |
| 6,406,792 B1 | 6/2002 | Briquet et al. |
| 6,437,083 B1 | 8/2002 | Brack et al. |
| 6,448,334 B1 | 9/2002 | Verhoogt et al. |
| 6,458,468 B1 | 10/2002 | Moskala et al. |
| 6,504,002 B1 | 1/2003 | Karlik et al. |
| 6,559,272 B1 | 5/2003 | Jeon et al. |
| 6,573,328 B2 | 6/2003 | Kropp et al. |
| 6,599,994 B2 | 7/2003 | Shelby et al. |
| 6,600,080 B1 | 7/2003 | Nagamura et al. |
| 6,639,067 B1 | 10/2003 | Brinegar et al. |
| 6,656,577 B1 | 12/2003 | Adelman et al. |
| 6,669,980 B2 | 12/2003 | Hansen |
| 6,723,768 B2 | 4/2004 | Adams et al. |
| 6,733,716 B2 | 5/2004 | Belcher |
| 6,740,377 B2 | 5/2004 | Pecorini et al. |
| 6,773,653 B2 | 8/2004 | Miller et al. |
| 6,818,293 B1 | 11/2004 | Keep et al. |

| | | |
|---|---|---|
| 6,818,730 B2 | 11/2004 | Brandenburg et al. |
| 6,846,440 B2 | 1/2005 | Flynn et al. |
| 6,846,508 B1 | 1/2005 | Colas et al. |
| 6,896,966 B2 | 5/2005 | Crawford et al. |
| 6,908,650 B2 | 6/2005 | Odorisio et al. |
| 6,914,120 B2 | 7/2005 | Germroth et al. |
| 6,919,489 B1 | 7/2005 | McCusker-Orth |
| 7,037,576 B2 | 5/2006 | Willham et al. |
| 7,048,978 B2 | 5/2006 | Tanaka et al. |
| 7,053,143 B2 | 5/2006 | Mori et al. |
| 7,122,661 B2 | 10/2006 | Fleche et al. |
| 7,169,880 B2 | 1/2007 | Shelby et al. |
| 7,297,755 B2 | 11/2007 | Shelby et al. |
| 7,354,628 B2 | 4/2008 | Steube |
| 7,375,154 B2 | 5/2008 | Stafford et al. |
| 7,427,430 B2 | 9/2008 | Rhee et al. |
| 7,468,409 B2 | 12/2008 | Pearson et al. |
| 7,482,397 B2 | 1/2009 | Pearson et al. |
| 2001/0029324 A1 | 10/2001 | Walker et al. |
| 2001/0031805 A1 | 10/2001 | Buhler |
| 2001/0034419 A1 | 10/2001 | Kanayama et al. |
| 2001/0044003 A1 | 11/2001 | Galluci et al. |
| 2002/0055586 A1 | 5/2002 | Dalgewicz, III et al. |
| 2002/0128357 A1 | 9/2002 | Goossens et al. |
| 2002/0132963 A1 | 9/2002 | Quillen |
| 2002/0137856 A1 | 9/2002 | Andrews et al. |
| 2002/0188092 A1 | 12/2002 | Moskala et al. |
| 2002/0198297 A1 | 12/2002 | Odorisio et al. |
| 2003/0032737 A1 | 2/2003 | Andrews et al. |
| 2003/0060546 A1 | 3/2003 | Moskala et al. |
| 2003/0075516 A1 | 4/2003 | Rothman et al. |
| 2003/0077546 A1 | 4/2003 | Donovan et al. |
| 2003/0135015 A1 | 7/2003 | Fujimaki et al. |
| 2003/0139497 A1 | 7/2003 | Odorisio et al. |
| 2003/0149177 A1 | 8/2003 | Andrews et al. |
| 2003/0169514 A1 | 9/2003 | Bourdelais et al. |
| 2003/0187151 A1 | 10/2003 | Adams et al. |
| 2003/0195295 A1 | 10/2003 | Mahood et al. |
| 2003/0221716 A1 | 12/2003 | Olson |
| 2003/0229181 A1 | 12/2003 | Hariharan et al. |
| 2004/0022526 A1 | 2/2004 | Kuno et al. |
| 2004/0063864 A1 | 4/2004 | Adams et al. |
| 2004/0101687 A1 | 5/2004 | Crawford et al. |
| 2004/0106707 A1 | 6/2004 | Su et al. |
| 2004/0106767 A1 | 6/2004 | Simon et al. |
| 2004/0108623 A1 | 6/2004 | Deeter et al. |
| 2004/0138381 A1 | 7/2004 | Blasius et al. |
| 2004/0145700 A1 | 7/2004 | Miniutti et al. |
| 2004/0164279 A1 | 8/2004 | Stevenson et al. |
| 2004/0202822 A1 | 10/2004 | Bourdelais et al. |
| 2004/0214984 A1 | 10/2004 | Keep et al. |
| 2005/0008885 A1 | 1/2005 | Blakely et al. |
| 2005/0072060 A1 | 4/2005 | Moncho et al. |
| 2005/0075466 A1 | 4/2005 | Oguro et al. |
| 2005/0096453 A1 | 5/2005 | Flynn et al. |
| 2005/0101759 A1 | 5/2005 | Odorisio et al. |
| 2005/0113556 A1 | 5/2005 | Strand et al. |
| 2005/0119359 A1 | 6/2005 | Shelby et al. |
| 2005/0124779 A1 | 6/2005 | Shelby et al. |
| 2005/0181155 A1 | 8/2005 | Share et al. |
| 2005/0209435 A1 | 9/2005 | Hirokane et al. |
| 2006/0004151 A1 | 1/2006 | Shaikh et al. |
| 2006/0036012 A1 | 2/2006 | Hayes et al. |
| 2006/0094858 A1 | 5/2006 | Turner et al. |
| 2006/0111481 A1 | 5/2006 | Pearson et al. |
| 2006/0111519 A1 | 5/2006 | Strand et al. |
| 2006/0135668 A1 | 6/2006 | Hayes |
| 2006/0146228 A1 | 7/2006 | Sogo et al. |
| 2006/0151907 A1 | 7/2006 | Kashiwabara |
| 2006/0180560 A1 | 8/2006 | Robinson |
| 2006/0197246 A1 | 9/2006 | Hale et al. |
| 2006/0199904 A1 | 9/2006 | Hale et al. |
| 2006/0199919 A1 | 9/2006 | Hale et al. |
| 2006/0228507 A1 | 10/2006 | Hale et al. |
| 2006/0234073 A1 | 10/2006 | Hale et al. |
| 2006/0235167 A1 | 10/2006 | Hale et al. |
| 2006/0241325 A1 | 10/2006 | Komplin et al. |
| 2006/0247388 A1 | 11/2006 | Hale et al. |
| 2006/0270773 A1 | 11/2006 | Hale et al. |
| 2006/0270806 A1 | 11/2006 | Hale |
| 2007/0049667 A1 | 3/2007 | Kim et al. |
| 2007/0071930 A1 | 3/2007 | Shelby et al. |
| 2008/0201910 A1 | 8/2008 | Schoening et al. |
| 2009/0123756 A1 | 5/2009 | Hashimoto et al. |

FOREIGN PATENT DOCUMENTS

| | | |
|---|---|---|
| EP | 0 595 413 A1 | 5/1994 |
| EP | 0 698 631 | 2/1996 |
| EP | 0 714 764 A2 | 6/1996 |
| EP | 0 902 052 A1 | 3/1999 |
| EP | 0 930 531 A1 | 7/1999 |
| EP | 1 035 167 A | 9/2000 |
| EP | 1 066 825 A1 | 1/2001 |
| EP | 1 674 496 A1 | 6/2006 |
| FR | 1278284 | 12/1961 |
| FR | 1291273 | 5/1965 |
| FR | 1432471 | 2/1966 |
| FR | 1434658 | 2/1966 |
| FR | 2112400 | 6/1972 |
| GB | 962913 | 7/1964 |
| GB | 1041651 | 9/1966 |
| GB | 1044015 | 9/1966 |
| GB | 1047043 | 11/1966 |
| GB | 1090241 | 11/1967 |
| GB | 1130558 | 10/1968 |
| GB | 1 278 284 | 6/1972 |
| GB | 1364732 | 8/1974 |
| GB | 2216919 A | 10/1989 |
| JP | 56-88440 A | 12/1979 |
| JP | 03207743 | 9/1991 |
| JP | 65-01040 | 2/1994 |
| JP | 9-59371 A | 4/1997 |
| JP | 11-222516 | 8/1999 |
| JP | 2001-066701 | 8/1999 |
| JP | 2000-352620 A | 12/2000 |
| JP | 2001-098086 | 4/2001 |
| JP | 2001-214049 | 8/2001 |
| JP | 2003292593 A | 10/2003 |
| JP | 2004-058565 A | 2/2004 |
| JP | 2004-066624 A | 3/2004 |
| JP | 2004-067973 A | 3/2004 |
| JP | 2004-244497 A | 9/2004 |
| JP | 2004-292558 A | 10/2004 |
| JP | 2005-254757 A | 9/2005 |
| JP | 2007-069914 A | 3/2007 |
| JP | 2007-253491 A | 10/2007 |
| KR | 2001-089942 | 10/2001 |
| KR | 2003-054611 | 7/2003 |
| WO | WO 97-01118 | 1/1997 |
| WO | WO 01-06981 | 2/2001 |
| WO | WO 01-85824 A2 | 11/2001 |
| WO | WO 02-055570 A1 | 7/2002 |
| WO | WO 02-059207 | 8/2002 |
| WO | WO2004-009146 A1 | 1/2004 |
| WO | WO 2004-039860 | 5/2004 |
| WO | WO 2004-104077 A1 | 12/2004 |
| WO | WO 2004-106988 A2 | 12/2004 |
| WO | WO 2005-007735 A2 | 1/2005 |
| WO | WO 2005-026241 A1 | 3/2005 |
| WO | WO 2006-025827 | 3/2006 |
| WO | WO 2006-127755 A2 | 11/2006 |
| WO | WO 2006-127831 A1 | 11/2006 |
| WO | WO 2007-053434 A1 | 5/2007 |
| WO | WO 2007-053548 A2 | 5/2007 |
| WO | WO 2007-053549 A1 | 5/2007 |
| WO | 2007/123631 A | 11/2007 |

OTHER PUBLICATIONS

Abstract of U.S. Defense Publication T875,010, 875 O.G. 342, Jun. 9, 1970.

Chen et al., "The molecular basis for the relationship between the secondary relaxation and mechanical properties of a series of polyester copolymer glasses," Marcromolecules, 32:5944-5955 (1999).

Kelsey, E. et al., "High Impact, Amorphous Terephthalate Copolyesters of Rigid 2,2,4,4-Tetramethyl-1,3-cyclobutanediol with Flexible Diols," Macromolecules, vol. 33, 2000, pp. 5810-5818, American Chemical Society.

"Plastic Additives Handbook," 5th Edition, 2001, pp. 98-108 and pp. 109-112 (Hanser Gardner Publications, Inc., Cincinnati, OH.

Scheirs, John, et al., "Modern Polyesters: Chemistry and Technology of Polyesters and Copolyesters," Technology & Engineering, 2003, p. 287.

English language Abstract of JP 02-305816 from Patent Abstracts of Japan, Dec. 19, 1990.

English language translation of Belgian Patent No. BE 615,850, Apr. 13, 1962.

English language translation of French Patent No. FR 1,432,471, Feb. 7, 1966.

English language translation of French Patent No. FR 1,434,658, Feb. 28, 1966.

U.S. Appl. No. 11/390,555, filed Mar. 28, 2006, Emmett Dudley Crawford, et al.

U.S. Appl. No. 11/390,563, filed Mar. 28, 2006, Emmett Dudley Crawford, et al.

U.S. Appl. No. 11/390,629, filed Mar. 28, 2006, Emmett Dudley Crawford, et al.

U.S. Appl. No. 11/390,630, filed Mar. 28, 2006, Emmett Dudley Crawford, et al.

U.S. Appl. No. 11/390,631, filed Mar. 28, 2006, Emmett Dudley Crawford, et al.

U.S. Appl. No. 11/390,654, filed Mar. 28, 2006, Emmett Dudley Crawford, et al.

U.S. Appl. No. 11/390,655, filed Mar. 28, 2006, Emmett Dudley Crawford, et al.

U.S. Appl. No. 11/390,671, filed Mar. 28, 2006, Emmett Dudley Crawford, et al.

U.S. Appl. No. 11/390,672, filed Mar. 28, 2006, Emmett Dudley Crawford, et al.

U.S. Appl. No. 11/390,722, filed Mar. 28, 2006, Emmett Dudley Crawford, et al.

U.S. Appl. No. 11/390,750, filed Mar. 28, 2006, Emmett Dudley Crawford, et al.

U.S. Appl. No. 11/390,751, filed Mar. 28, 2006, Emmett Dudley Crawford, et al.

U.S. Appl. No. 11/390,752, filed Mar. 28, 2006, Emmett Dudley Crawford, et al.

U.S. Appl. No. 11/390,773, filed Mar. 28, 2006, Emmett Dudley Crawford, et al.

U.S. Appl. No. 11/390,793, filed Mar. 28, 2006, Emmett Dudley Crawford, et al.

U.S. Appl. No. 11/390,794, filed Mar. 28, 2006, Emmett Dudley Crawford, et al.

U.S. Appl. No. 11/390,809, filed Mar. 28, 2006, Wesley Raymond Hale, et al.

U.S. Appl. No. 11/390,811, filed Mar. 28, 2006, Emmett Dudley Crawford, et al.

U.S. Appl. No. 11/390,812, filed Mar. 28, 2006, Wesley Raymond Hale, et al.

U.S. Appl. No. 11/390,814, filed Mar. 28, 2006, Emmett Dudley Crawford, et al.

U.S. Appl. No. 11/390,826, filed Mar. 28, 2006, Emmett Dudley Crawford, et al.

U.S. Appl. No. 11/390,827, filed Mar. 28, 2006, Emmett Dudley Crawford, et al.

U.S. Appl. No. 11/390,836, filed Mar. 28, 2006, Emmett Dudley Crawford, et al.

U.S. Appl. No. 11/390,846, filed Mar. 28, 2006, Wesley Raymond Hale, et al.

U.S. Appl. No. 11/390,847, filed Mar. 28, 2006, Emmett Dudley Crawford, et al.

U.S. Appl. No. 11/390,853, filed Mar. 28, 2006, Emmett Dudley Crawford, et al.

U.S. Appl. No. 11/390,858, filed Mar. 28, 2006, Emmett Dudley Crawford, et al.

U.S. Appl. No. 11/390,864, filed Mar. 28, 2006, Wesley Raymond Hale, et al.

U.S. Appl. No. 11/390,865, filed Mar. 28, 2006, Emmett Dudley Crawford, et al.

U.S. Appl. No. 11/390,882, filed Mar. 28, 2006, Emmett Dudley Crawford, et al.

U.S. Appl. No. 11/390,883, filed Mar. 28, 2006, Thomas Joseph Pecorini, et al.

U.S. Appl. No. 11/390,908, filed Mar. 28, 2006, Wesley Raymond Hale, et al.

U.S. Appl. No. 11/391,063, filed Mar. 28, 2006, Emmett Dudley Crawford, et al.

U.S. Appl. No. 11/391,124, filed Mar. 28, 2006, Wesley Raymond Hale, et al.

U.S. Appl. No. 11/391,125, filed Mar. 28, 2006, Emmett Dudley Crawford, et al.

U.S. Appl. No. 11/391,137, filed Mar. 28, 2006, Emmett Dudley Crawford, et al.

U.S. Appl. No. 11/391,156, filed Mar. 28, 2006, Emmett Dudley Crawford, et al.

U.S. Appl. No. 11/391,485, filed Mar. 28, 2006, Emmett Dudley Crawford, et al.

U.S. Appl. No. 11/391,495, filed Mar. 28, 2006, Emmett Dudley Crawford, et al.

U.S. Appl. No. 11/391,505, filed Mar. 28, 2006, Emmett Dudley Crawford, et al.

U.S. Appl. No. 11/391,565, filed Mar. 28, 2006, Emmett Dudley Crawford, et al.

U.S. Appl. No. 11/391,571, filed Mar. 28, 2006, Emmett Dudley Crawford, et al.

U.S. Appl. No. 11/391,576, filed Mar. 28, 2006, Emmett Dudley Crawford, et al.

U.S. Appl. No. 11/391,642, filed Mar. 28, 2006, Emmett Dudley Crawford, et al.

U.S. Appl. No. 11/391,659, filed Mar. 28, 2006, Emmett Dudley Crawford, et al.

U.S. Appl. No. 11/588,524, filed Oct. 27, 2006, Emmett Dudley Crawford, et al.

U.S. Appl. No. 11/588,458, filed Oct. 27, 2006, Emmett Dudley Crawford, et al.

U.S. Appl. No. 11/588,907, filed Oct. 27, 2006, Emmett Dudley Crawford, et al.

U.S. Appl. No. 11/588,527, filed Oct. 27, 2006, Emmett Dudley Crawford, et al.

U.S. Appl. No. 11/588,906, filed Oct. 27, 2006, Ted Calvin Germroth, et al.

U.S. Appl. No. 11/588,883, filed Oct. 27, 2006, Ted Calvin Germroth, et al.

U.S. Appl. No. 11/588,554, filed Oct. 27, 2006, Emmett Dudley Crawford, et al.

U.S. Appl. No. 11/635,434, filed Dec. 7, 2006, Emmett Dudley Crawford.

U.S. Appl. No. 11/635,433, filed Dec. 7, 2006, Emmett Dudley Crawford.

U.S. Appl. No. 11/439,062, filed May 23, 2006, Wesley Raymond Hale, et al.

U.S. Appl. No. 11/439,340, filed May 23, 2006, Wesley Raymond Hale.

U.S. Appl. No. 11/706,476, filed Feb. 14, 2007, Leslie Shane Moody, et al.

U.S. Appl. No. 11/706,791, filed Feb. 14, 2007, Leslie Shane Moody, et al.

U.S. Appl. No. 12/091,568, filed Apr. 25, 2008, Emmett Dudley Crawford, et al.

U.S. Appl. No. 12/091,566, filed Apr. 25, 2008, Emmett Dudley Crawford, et al.

U.S. Appl. No. 12/091,570, filed Apr. 25, 2008, Ted Calvin Germroth, et al.

U.S. Appl. No. 12/091,572, filed Apr. 25, 2008, Ted Calvin Germroth, et al.

U.S. Appl. No. 12/294,690, filed Sep. 26, 2008, Ted Calvin Germroth et al.

U.S. Appl. No. 12/294,686, filed Sep. 26, 2008, Ted Calvin Germroth et al.

U.S. Appl. No. 12/274,692, filed Nov. 20, 2008, Thomas Joseph Pecorini et al.

U.S. Appl. No. 12/338,453, filed Dec. 18, 2008, Emmett Dudley Crawford, et al.

U.S. Appl. No. 12/361,779, filed Jan. 29, 2009, Emmett Dudley Crawford.
U.S. Appl. No. 12/365,515, filed Feb. 4, 2009, Emmett Dudley Crawford.
Chapter 4—Processing of Plastics in "*Plastics Engineering, 3rd ed*", R.J. Crawford, Butterworth-Heinemann Publisher, 1998, Oxford, England, pp. 245-342.
Fox equation (T.G. Fox, Session J, Bull. Am. Phys. Soc., 1, 123 (1956)).
*The Technology of Plasticizers*, by J. Kern Sears and Joseph R Darby, published by Society of Plastic Engineers—Wiley and Sons, New York, 1982; pp. 136-139.
Coleman et al., "Polymer Reviews—A Practical Guide to Polymer Miscibility," *Polymer 31*, pp. 1187-1203 (1990).
"*Hansen Solubility Parameters, a Users Handbook*", by Charles M. Hansen, Chapter 1, CRC Press, 2000, pp. 1-24.
Martinez et al., "*Phase Behavior and Mechanical Properties of Injection Molded Poly (Ethylene Terephthalate)—Polyarylate Blends*"; Journal of Applied Polymer Science, John Wiley and Sons Inc. New York, US, vol. 45, No. 7, Jul. 5, 1992, p. 1135-1143.
Won Ho Jo et al. : :*Miscibility of poly(ether imide)-poly(ethylene terephthalate) blends*; Polymer Bulletin, Springer, Heidelberg, DE, vol. 33, No. 1, Jun. 1, 1994, p. 113-118 (1994).
Anonymous: "*Poly (ethylene naphthalenedicarboxylate)-polyetherimide blends*" Research Disclosure, Mason Publications, Hampshire, GB, vol. 283, No. 38, Nov. 1987.
ASTM D1525-06, *Standard Test Method for Vicat Softening Temperature of Plastics*, Mar. 15, 2006.
ASTM D648-06, *Standard Test Method for Deflection Temperature of Plastics Under Flexural Load in the Edgewise Position*, Mar. 15, 2006.
ASTM D256-06, *Standard Test Methods for Determining the Izod Pendulum Impact Resistance of Plastics*, Mar. 15, 2006.
ASTM D790-03, *Standard Test Methods for Flexural Properties of Unreinforced and Reinforced Plastics and Electrical Insulating Materials*, Mar. 10, 2003.
ASTM D638-03, *Standard Test Method for Tensile Properties of Plastics*, Dec. 1, 2003.
ASTM D3418-03, *Transition Temperatures and Enthalpies of Fusion and Crystallization of Polymers by Differential Scanning Calorimetry*, Dec. 1, 2003.
Database WPI, Section Ch, Week 200536, Derwent Publications Ltd., London, GB; AN 2005-355258, XP002396922 & WO 2005-030833 A1 (Kanebo Ltd) Apr. 7, 2005 abstract.
Shearer, N.H., "T18-Type 1 Polyesters," Mar. 1966, SPE Annual Technical Conference and Exhibition, XP009080224.
Gachter, Muller, "Taschenbuch der Kunststoff-Additive," 1990, Carl Hanser Verlag Munchen Wien, XP02450422, pp. 96-97.
Gachter, Muller, "Kunstoff-Additive," 1990, Carl Hanser Verlag Munchen Wien, XP 02449987, pp. 96-99.
Brown, R., "Taschenbuch Kunstoff-Additive", 1990, Carl Hanswer Verlag Munchen Wiel, XP002455247, pp. 361-363.
Chang, S. et al., "Effect of Stabilizers on the Preparation of Poly(ethylene Terephthalate)", Journal of Polymer Science, Polymer Chemistry Edition, 1982, vol. 20, pp. 2053-2061, John Wiley & Sons, Inc.
USPTO Office Action dated Mar. 11, 2008 for copending U.S. Appl. No. 11/391,642.
USPTO Office Action dated Mar. 24, 2008 for copending U.S. Appl. No. 11/390,908.
USPTO Office Action dated Apr. 15, 2008 for copending U.S. Appl. No. 11/390,629.
USPTO Office Action dated Apr. 16, 2008 for copending U.S. Appl. No. 11/390,751.
USPTO Office Action dated Apr. 17, 2008 for copending U.S. Appl. No. 11/390,814.
USPTO Office Action dated Jun. 3, 2008 for copending U.S. Appl. No. 11/391,063.
USPTO Office Action dated Sep. 10, 2008 for copending U.S. Appl. No. 11/390,752.
USPTO Office Action dated Sep. 10, 2008 for copending U.S. Appl. No. 11/390,794.
USPTO Office Action dated Sep. 19, 2008 for copending U.S. Appl. No. 11/391,565.
USPTO Office Action dated Oct. 2, 2008 for copending U.S. Appl. No. 11/390,671.
USPTO Office Action dated Sep. 24, 2008 for copending U.S. Appl. No. 11/390,631.
USPTO Office Action dated Oct. 1, 2008 for copending U.S. Appl. No. 11/390,655.
USPTO Office Action dated Sep. 29, 2008, for copending U.S. Appl. No. 11/391,137.
USPTO Office Action dated Sep. 9, 2008 for copending U.S. Appl. No. 11/391,571.
USPTO Office Action dated Oct. 22, 2008 for copending U.S. Appl. No. 11/391,125.
USPTO Office Action dated Oct. 20, 2008 for copending U.S. Appl. No. 11/390,672.
USPTO Office Action dated Oct. 8, 2008 for copending U.S. Appl. No. 11/390,853.
USPTO Office Action dated Oct. 9, 2008 for copending U.S. Appl. No. 11/391,505.
USPTO Notice of Allowance dated Oct. 7, 2008 for copending U.S. Appl. No. 11/390,908.
USPTO Office Action dated Oct. 14, 2008 for copending U.S. Appl. No. 11/390,811.
USPTO Office Action dated Oct. 22, 2008 for copending U.S. Appl. No. 11/390,750.
USPTO Office Action dated Oct. 22, 2008 for copending U.S. Appl. No. 11/390,865.
USPTO Office Action dated Oct. 14, 2008 for copending U.S. Appl. No. 11/390,654.
USPTO Office Action dated Oct. 20, 2008 for copending U.S. Appl. No. 11/390,836.
Copending U.S. Appl. No. 12/254,894, filed Oct. 21, 2008, Gary Michael Stack, et al.
Copending U.S. Appl. No. 12/390,694, filed Feb. 23, 2009, Gary Michael Stack.
USPTO Office Action dated Oct. 29, 2008 for copending U.S. Appl. No. 11/390,955.
USPTO Notice of Allowance dated Nov. 3, 2008 for copending U.S. Appl. No. 11/391,642.
USPTO Office Action dated Nov. 3, 2008 for copending U.S. Appl. No. 11/391,485.
USPTO Office Action dated Oct. 29, 2008 for copending U.S. Appl. No. 11/390,864.
USPTO Office Action dated Oct. 30, 2008 for copending U.S. Appl. No. 11/391,495.
USPTO Office Action dated Oct. 31, 2008 for copending U.S. Appl. No. 11/391,156.
USPTO Office Action dated Nov. 3, 2008 for copending U.S. Appl. No. 11/390,883.
USPTO Office Action dated Dec. 19, 2008 for copending U.S. Appl. No. 11/390,751.
USPTO Office Action dated Dec. 31, 2008 for copending U.S. Appl. No. 11/390,827.
USPTO Office Action dated Dec. 31, 2008 for copending U.S. Appl. No. 11/390,826.
USPTO Office Action dated Nov. 14, 2008 for copending U.S. Appl. No. 11/390,630.
USPTO Office Action dated Dec. 19, 2008 for copending U.S. Appl. No. 11/391,576.
USPTO Office Action dated Dec. 19, 2008 for copending U.S. Appl. No. 11/390,629.
USPTO Office Action dated Dec. 31, 2008 for copending U.S. Appl. No. 11/390,773.
USPTO Office Action dated Dec. 12, 2008 for copending U.S. Appl. No. 11/391,063.
USPTO Office Action dated Dec. 19, 2008 for copending U.S. Appl. No. 11/390,814.
USPTO Office Action dated Dec. 31, 2008 for copending U.S. Appl. No. 11/390,722.
USPTO Office Action dated Nov. 14, 2008 for copending U.S. Appl. No. 11/390,882.
USPTO Office Action dated Jan. 29, 2009 for copending U.S. Appl. No. 11/588,524.

USPTO Office Action dated Jan. 30, 2009 for copending U.S. Appl. No. 11/588,458.
USPTO Office Action dated Feb. 2, 2009 for copending U.S. Appl. No. 11/390,853.
USPTO Office Action dated Jan. 21, 2009 for copending U.S. Appl. No. 11/390,847.
USPTO Office Action dated Jan. 12, 2009 for copending U.S. Appl. No. 11/390,858.
USPTO Office Action dated Jan. 26, 2009 for copending U.S. Appl. No. 11/391,659.
USPTO Office Action dated Jan. 26, 2009 for copending U.S. Appl. No. 11/588,554.
USPTO Office Action dated Feb. 3, 2009 for copending U.S. Appl. No. 11/391,505.
USPTO Office Action dated Feb. 10, 2009 for copending U.S. Appl. No. 11/390,865.
USPTO Office Action dated Feb. 12, 2009 for copending U.S. Appl. No. 11/439,062.
USPTO Office Action dated Feb. 13, 2009 for copending U.S. Appl. No. 11/439,340.
USPTO Office Action dated Feb. 25, 2009 for copending U.S. Appl. No. 11/588,907.
USPTO Office Action dated Feb. 25, 2009 for copending U.S. Appl. No. 11/588,527.
USPTO Office Action dated Feb. 27, 2009 for copending U.S. Appl. No. 11/390,955.
USPTO Office Action dated Feb. 25, 2009 for copending U.S. Appl. No. 11/588,906.
USPTO Office Action dated Feb. 25, 2009 for copending U.S. Appl. No. 11/588,883.
USPTO Office Action dated Mar. 5, 2009 for copending U.S. Appl. No. 11/390,864.
USPTO Office Action dated Mar. 6, 2009 for copending U.S. Appl. No. 11/391,156.
USPTO Office Action dated Feb. 25, 2009 for copending U.S. Appl. No. 11/390,811.
USPTO Office Action dated Feb. 27, 2009 for copending U.S. Appl. No. 11/390,654.
USPTO Office Action dated Feb. 27, 2009 for copending U.S. Appl. No. 11/390,836.
USPTO Office Action dated Mar. 13, 2009 for copending U.S. Appl. No. 11/390,883.
USPTO Office Action dated Mar. 11, 2009 for copending U.S. Appl. No. 11/390,630.
USPTO Office Action dated Mar. 9, 2009 for copending U.S. Appl. No. 11/391,495.
USPTO Office Action dated Mar. 9, 2009 for copending U.S. Appl. No. 11/390,750.
USPTO Office Action dated Mar. 16, 2009 for copending U.S. Appl. No. 11/390,882.
USPTO Office Action dated Apr. 27, 2009 for copending U.S. Appl. No. 11/390,655.
USPTO Office Action dated Apr. 27, 2009 for copending U.S. Appl. No. 11/391,137.
USPTO Office Action dated Mar. 16, 2009 for copending U.S. Appl. No. 11/391,485.
USPTO Office Action dated Apr. 15, 2009 for copending U.S. Appl. No. 12/091,566.
USPTO Notice of Allowance dated Apr. 13, 2009 for copending U.S. Appl. No. 11/391,063.
USPTO Office Action dated Apr. 16, 2009 for copending U.S. Appl. No. 12/091,570.
USPTO Office Action dated Apr. 17, 2009 for copending U.S. Appl. No. 11/390,671.
USPTO Office Action dated Apr. 17, 2009 for copending U.S. Appl. No. 11/391,565.
USPTO Office Action dated Apr. 20, 2009 for copending U.S. Appl. No. 11/390,631.
USPTO Office Action dated Mar. 31, 2009 for copending U.S. Appl. No. 11/390,563.
USPTO Office Action dated Apr. 2, 2009 for copending U.S. Appl. No. 11/390,793.
USPTO Office Action dated Mar. 23, 2009 for copending U.S. Appl. No. 11/390,752.
USPTO Office Action dated Mar. 23, 2009 for copending U.S. Appl. No. 11/390,794.
USPTO Office Action dated May 13, 2009 for copending U.S. Appl. No. 12/361,779.
USPTO Office Action dated May 13, 2009 for copending U.S. Appl. No. 12/365,515.
USPTO Office Action dated May 21, 2009 for copending U.S. Appl. No. 11/706,476.
USPTO Office Action dated May 22, 2009 for copending U.S. Appl. No. 11/706,791.
USPTO Office Action dated May 18, 2009 for copending U.S. Appl. No. 11/391,505.
USPTO Office Action dated Apr. 14, 2009 for copending U.S. Appl. No. 11/635,434.
USPTO Office Action dated Apr. 14, 2009 for copending U.S. Appl. No. 11/635,433.
USPTO Office Action dated May 18, 2009 for copending U.S. Appl. No. 11/390,846.
USPTO Office Action dated Jun. 11, 2009 for copending U.S. Appl. No. 11/390,809.
USPTO Office Action dated Jul. 2, 2009 for copending U.S. Appl. No. 11/390,827.
USPTO Office Action dated Aug. 7, 2009 for copending U.S. Appl. No. 11/390,773.
USPTO Office Action dated Aug. 27, 2009 for copending U.S. Appl. No. 11/390,826.
USPTO Office Action dated Aug. 10, 2009 for copending U.S. Appl. No. 11/390,722.
Dixon, E.R. et al., "The Inter-Relation of Some Mechanical Properties with Molecular Weight and Crystallinity in Poly(ethylene terephthalate)", 1968, pp. 464-470, Journal of Materials Science, vol. 3.
USPTO Office Action dated Sep. 4, 2009, for copending U.S. Appl. No. 11/391,124.
USPTO Office Action dated Sep. 10, 2009, for copending U.S. Appl. No. 11/390,812.
New Copending U.S. Appl. No. 12/479,893, filed Jun. 8, 2009, Emmett Dudley Crawford, et al.
USPTO Office Action dated Sep. 14, 2009 for copending U.S. Appl. No. 11/391,576.
Ellis, Thomas S., "Miscibility of Polyamide Blends: Effects of Configuration," 1995, Polymer, vol. 36, Issue 20, pp. 3919-3926.
Buschow, K.H.J., et al., "Packaging: Papers for Sacks and Bags," 2001, Encyclopedia of Materials: Science and Technology, vol. 8, Elsevier, pp. 6646-6652.
Coles, Richard, et al., "Food Packaging Technology," 2003, pp. 194-195 and 224-229, Blackwell Publishing.
Sajiki, Junko, et al., "Leaching of Bisphenol A (BPA) to Seawater from Polycarbonate Plastic and its Degradation by Reactive Oxygen Species," 2003, Chemosphere, 51, pp. 55-62.
USPTO Office Action dated Oct. 2, 2009 for copending U.S. Appl. No. 11/588,524.
USPTO Office Action dated Oct. 7, 2009 for copending U.S. Appl. No. 11/588,458.
USPTO Office Action dated Sep. 29, 2009 for copending U.S. Appl. No. 11/390,751.
USPTO Office Action dated Sep. 24, 2009 for copending U.S. Appl. No. 11/588,883.
USPTO Office Action dated Sep. 28, 2009 for copending U.S. Appl. No. 11/390,847.
USPTO Office Action dated Sep. 24, 2009 for copending U.S. Appl. No. 11/390,858.
USPTO Office Action dated Sep. 29, 2009 for copending U.S. Appl. No. 11/390,629.
USPTO Office Action dated Sep. 29, 2009 for copending U.S. Appl. No. 11/390,814.
USPTO Office Action dated Oct. 19, 2009 for copending U.S. Appl. No. 11/390,563.
USPTO Office Action dated Oct. 20, 2009 for copending U.S. Appl. No. 11/588,907.

USPTO Office Action dated Oct. 21, 2009 for copending U.S. Appl. No. 11/391,156.
Gupta, V.B. et al., "PET Fibers, Films, and Bottles: Section 5-7", Handbook of Thermoplastic Polyesters: Homopolymers, Copolymers, Blends, and Composites, 2005, pp. 362-388, Wiley InterScience.
USPTO Office Action dated Oct. 22, 2009 for copending U.S. Appl. No. 11/588,906.
USPTO Office Action dated Nov. 3, 2009 for copending U.S. Appl. No. 11/390,883.
USPTO Office Action dated Nov. 4, 2009 for copending U.S. Appl. No. 11/390,750.
USPTO Office Action dated Nov. 4, 2009 for copending U.S. Appl. No. 11/390,864.
USPTO Office Action dated Nov. 17, 2009 for copending U.S. Appl. No. 12/254,894.
USPTO Office Action dated Nov. 18, 2009 for copending U.S. Appl. No. 11/390,630.
USPTO Office Action dated Nov. 30, 2009 for copending U.S. Appl. No. 11/391,495.
Turner, S.R., et al., "Amorphous and Crystalline Polyesters based on 1,4-Cyclohexanedimethanol", Chapter 7, Modern Polyesters: Chemistry and Technology of Polyesters and Copolyesters, Edited by J. Sheirs and T.E. Long, 2003 John Wiley & Sons, Ltd., pp. 267-292.
USPTO Office Action dated Nov. 18, 2009 for copending U.S. Appl. No. 11/390,794.
USPTO Office Action dated Nov. 20, 2009 for copending U.S. Appl. No. 11/391,485.
USPTO Office Action dated Nov. 20, 2009 for copending U.S. Appl. No. 11/390,882.
USPTO Office Action dated Dec. 1, 2009 for copending U.S. Appl. No. 12/091,570.
USPTO Office Action dated Dec. 3, 2009 for copending U.S. Appl. No. 11/395,505.
USPTO Office Action dated Dec. 4, 2009 for copending U.S. Appl. No. 12/091,566.
Zipper, Marcus D.,et al., "A Free Volume Study of Miscible Polyester Blends," 1995, pp. 127-136, Polymer International, vol. 36.
"APEC High-Heat Polycarbonate Resin," 2004, Bayer Material Science Product Information *Not Prior Art; Submitted for State of the Art.*
Lobo, Hubert et al, "Handbook of Plastics Analysis," 2003, pp. 20 and 21, Marcel Dekker, Inc.
USPTO Notice of Allowance dated Dec. 11, 2009 for copending U.S. Appl. No. 12/365,515.
USPTO Office Action dated Dec. 18, 2009 for copending U.S. Appl. No. 11/390,846.
Copending U.S. Appl. No. 12/639,324, filed Dec. 16, 2009.
USPTO Notice of Allowance dated Dec. 22, 2009 for copending U.S. Appl. No. 12/361,779.
USPTO Office Action dated Jan. 7, 2010 for copending U.S. Appl. No. 12/091,568.
USPTO Office Action dated Jan. 13, 2010 for copending U.S. Appl. No. 11/635,433.
USPTO Office Action dated Jan. 14, 2010 for copending U.S. Appl. No. 11/390,809.
USPTO Notice of Allowance dated Jan. 27, 2010 for copending U.S. Appl. No. 11/635,434.
USPTO Office Action dated Mar. 11, 2010, for copending U.S. Appl. No. 11/391,124.
Copending U.S. Appl. No. 12/724,492, filed Mar. 16, 2010.
Copending U.S. Appl. No. 12/724,480, filed Mar. 16, 2010.
Copending U.S. Appl. No. 12/724,468, filed Mar. 16, 2010.
USPTO Office Action dated Mar. 19, 2010, for copending U.S. Appl. No. 11/588,527.
USPTO Notice of Allowance dated Mar. 24, 2010 for copending U.S. Appl. No. 11/391,565.
USPTO Office Action dated Mar. 29, 2010 for copending U.S. Appl. No. 11/390,812.
USPTO Notice of Allowance dated Apr. 15, 2010 for copending U.S. Appl. No. 11/391,505.
USPTO Office Action dated Apr. 19, 2010 for copending U.S. Appl. No. 12/724,480.
USPTO Office Action dated Apr. 21, 2010 for copending U.S. Appl. No. 12/724,468.
USPTO Office Action dated Apr. 21, 2010 for copending U.S. Appl. No. 12/724,492.
USPTO Office Action dated May 6, 2010 for copending U.S. Appl. No. 12/254,894.
New copending U.S. Appl. No. 12/784,193, filed May 20, 2010, Emmett Dudley Crawford, et al.
USPTO Notice of Allowance dated May 13, 2010 for copending U.S. Appl. No. 11/390,629.
USPTO Notice of Allowance dated May 13, 2010 for copending U.S. Appl. No. 11/390,751.
USPTO Notice of Allowance dated May 21, 2010 for copending U.S. Appl. No. 11/391,156.
USPTO Notice of Allowance dated May 26, 2010 for copending U.S. Appl. No. 11/391,495.
USPTO Notice of Allowance dated Jun. 24, 2010 for copending U.S. Appl. No. 11/391,576.
USPTO Office Action dated Jun. 24, 2010 for copending U.S. Appl. No. 11/390,846.
USPTO Office Action dated Jul. 8, 2010 for copending U.S. Appl. No. 11/390,809.
USPTO Notice of Allowance dated Jul. 8, 2010 for copending U.S. Appl. No. 11/390,630.
USPTO Notice of Allowance dated Jul. 8, 2010 for copending U.S. Appl. No. 11/390,883.
USPTO Office Action dated Jul. 12, 2010 for copending U.S. Appl. No. 11/390,794.
Notice of Allowance dated Jul. 13, 2010 for copending U.S. Appl. No. 11/391,505.
USPTO Office Action dated Jul. 22, 2010 for copending U.S. Appl. No. 12/479,893.
USPTO Notice of Allowance dated Jul. 22, 2010 for copending U.S. Appl. No. 11/391,485.
USPTO Notice of Allowance dated Aug. 3, 2010 for copending U.S. Appl. No. 11/390,864.
USPTO Office Action dated Aug. 6, 2010 for copending U.S. Appl. No. 11/773,275.
New copending U.S. Appl. No. 12/853,717, filed Aug. 10, 2010, Emmett Dudley Crawford, et al.
USPTO Notice of Allowance dated Aug. 11, 2010 for copending U.S. Appl. No. 11/390,631.
USPTO Notice of Allowance dated Sep. 2, 2010 for copending U.S. Appl. No. 11/390,811.
USPTO Office Action dated Sep. 2, 2010 for copending U.S. Appl. No. 11/391,124.
New copending U.S. Appl. No. 12/888,648, filed Sep. 23, 2010, Thomas Joseph Pecorini et al.
USPTO Office Action dated Oct. 5, 2010 for copending U.S. Appl. No. 11/390,655.
New copending U.S. Appl. No. 12/900,060, filed Oct. 7, 2010, Thomas Joseph Pecorini, et al.
USPTO Office Action dated Oct. 8, 2010 for copending U.S. Appl. No. 11/390,812.
USPTO Notice of Allowance dated Oct. 28, 2010 for copending U.S. Appl. No. 11/390,827.
USPTO Office Action dated Oct. 27, 2010 for copending U.S. Appl. No. 12/294,690.
New Copending U.S. Appl. No. 12/900,060, filed Oct. 7, 2010, Joseph Thomas Pecorini.
USPTO Notice of Allowance dated Oct. 14, 2010 for copending U.S. Appl. No. 11/390,722.
USPTO Notice of Allowance dated Nov. 2, 2010 for copending U.S. Appl. No. 12/724,480.
USPTO Notice of Allowance dated Nov. 4, 2010 for copending U.S. Appl. No. 12/724,468.
USPTO Notice of Allowance dated Nov. 4, 2010 for copending U.S. Appl. No. 11/390,955.
USPTO Office Action dated Nov. 4, 2010 for copending U.S. Appl. No. 12/294,686.
USPTO Notice of Allowance dated Nov. 4, 2010 for copending U.S. Appl. No. 11/390,826.

USPTO Office Action dated Oct. 27, 2010 for copending U.S. Appl. No. 11/390,836.
USPTO Notice of Allowance dated Nov. 23, 2010 for copending U.S. Appl. No. 11/390,563.
New copending U.S. Appl. No. 12/943,217, filed Nov. 10, 2010, Emmett Dudley Crawford et al.
New copending U.S. Appl. No. 12/963,698, filed Dec. 9, 2010.
New copending U.S. Appl. No. 13/007,838, filed Jan. 17, 2011, Emmett Dudley Crawford et al.
USPTO Office Action dated Jan. 24, 2011 for copending U.S. Appl. No. 11/773,275.
New copending U.S. Appl. No. 13/016,147, filed Jan. 28, 2011, Emmett Dudley Crawford, et al.
New copending U.S. Appl. No. 13/017,069, filed Jan. 31, 2011, Emmett Dudley Crawford, et al.
New Copending U.S. Appl. No. 13/017,352, filed Jan. 31, 2011, Emmett Dudley Crawford, et al.
USPTO Office Action dated Jan. 25, 2011 for copending U.S. Appl. No. 12/853,717.
Al-Malaika, S., "Stabilization", Encyclopedia of Polymer Science and Technology, vol. 4, 2001, pp. 179-229, John Wiley & Sons, Inc.
USPTO Notice of Allowance dated Jan. 26, 2011 for copending U.S. Appl. No. 11/390,858.
USPTO Office Action dated Feb. 2, 2011 for copending U.S. Appl. No. 11/390,655.
USPTO Office Action dated Mar. 17, 2011 for copending U.S. Appl. No. 12/479,893.
USPTO Notice of Allowance dated Mar. 17, 2011 for copending U.S. Appl. No. 11/391,137.
USPTO Office Action dated Feb. 14, 2011 for copending U.S. Appl. No. 12/294,690.
USPTO Notice of Allowance dated Feb. 18, 2011 for copending U.S. Appl. No. 11/390,809.
USPTO Notice of Allowance dated Feb. 17, 2011 for copending U.S. Appl. No. 11/390,812.
New Copending U.S. Appl. No. 13/097,701, filed Apr. 29, 2011, Michael Eugene Donelson, et al.
USPTO Office Action dated Jun. 2, 2011 for copending U.S. Appl. No. 12/338,453.
USPTO Office Action dated Jun. 16, 2011 for copending U.S. Appl. No. 12/390,694.
USPTO Notice of Allowance dated Aug. 12, 2011 for copending U.S. Appl. No. 11/390,752.
USPTO Office Action dated Jul. 19, 2011 for copending U.S. Appl. No. 11/390,794.
USPTO Notice of Allowance dated Jul. 21, 2011 for copending U.S. Appl. No. 11/390,671.
USPTO Notice of Allowance dated Aug. 3, 2011 for copending U.S. Appl. No. 11/390,655.
New copending U.S. Appl. No. 13/162,870, filed Jun. 17, 2011, Emmett Dudley Crawford, et al.
USPTO Office Action dated Jul. 7, 2011 for copending U.S. Appl. No. 11/588,906.
USPTO Office Action dated Jun. 22, 2011 for copending U.S. Appl. No. 12/091,570.
USPTO Office Action dated Jun. 8, 2011 for copending U.S. Appl. No. 11/588,883.
USPTO Office Action dated Aug. 17, 2011 for copending U.S. Appl. No. 12/274,692.
New copending U.S. Appl. No. 13/215,511, filed Aug. 23, 2011, Emmett Dudley Crawford, et al.
USPTO Office Action dated Sep. 14, 2011 for copending U.S. Appl. No. 13/017,069.
USPTO Notice of Allowance dated Sep. 16, 2011 for copending U.S. Appl. No. 11/390,671.
USPTO Notice of Allowance dated Sep. 16, 2011 for copending U.S. Appl. No. 12/784,193.
USPTO Office Action dated Oct. 17, 2011 for copending U.S. Appl. No. 12/853,717.
USPTO Notice of Allowance dated Oct. 17, 2011 for copending U.S. Appl. No. 11/390,794.
USPTO Notice of Allowance dated Oct. 25, 2011 for copending U.S. Appl. No. 12/900,060.
USPTO Office Action dated Oct. 31, 2011 for copending U.S. Appl. No. 12/639,324.
USPTO Office Action dated Nov. 2, 2011 for copending U.S. Appl. No. 12/479,893.
USPTO Notice of Allowance dated Nov. 2, 2011 for copending U.S. Appl. No. 12/390,694.
USPTO Notice of Allowance dated Nov. 10, 2011 for copending U.S. Appl. No. 12/943,217.
USPTO Notice of Allowance dated Nov. 28, 2011 for copending U.S. Appl. No. 12/274,692.
New copending U.S. Appl. No. 13/330,052, filed Dec. 19, 2011, Kenny Randolph Parker, et al.
USPTO Notice of Allowance dated Dec. 20, 2011 for copending U.S. Appl. No. 12/390,694.
USPTO Office Action dated Dec. 21, 2011 for copending U.S. Appl. No. 12/091,570.
New copending U.S. Appl. No. 13/348,677, filed Jan. 12, 2012, Emmett Dudley Crawford, et al.
USPTO Notice of Allowance dated Feb. 14, 2012 for copending U.S. Appl. No. 11/588,906.
New copending U.S. Appl. No. 13/398,262, filed Feb. 26, 2012, Emmett Dudley Crawford, et al.
Hasek, et al. Chemistry of Dimethylketone Dimer. Journal of Organic Chemistry, 1961, vol. 26, pp. 700-704.
Sprague et al., Hydrogentation and Hydrogenolysis of 1,3-Diketones. Journal of the American Chemical Society, 1934, vol. 56, pp. 2669-2675.
Coover, H. et al., "Copolyester Molding Compositions," Chemical Abstracts Service, XP002391844, 1970.
Bergen, R. L., Jr., "Stress Cracking of Rigid Thermoplastics," SPE Journal, pp. 667-669, Jun. 1962.
2866-43-5. Registry [>database>online].  Chemical Abstracts Services, a division of the American Chemical Society [retrieved on Nov. 6, 2006]. Retrieved from: SciFinder.
7128-64-5. Registry [>database>online]. Chemical Abstracts Services, a division of the American Chemical Society [retrieved on Nov. 6, 2006]. Retrieved from: SciFinder.

Hydrogenation of 2,2,4,4-Tetraalkycyclobutane-1,3-dione
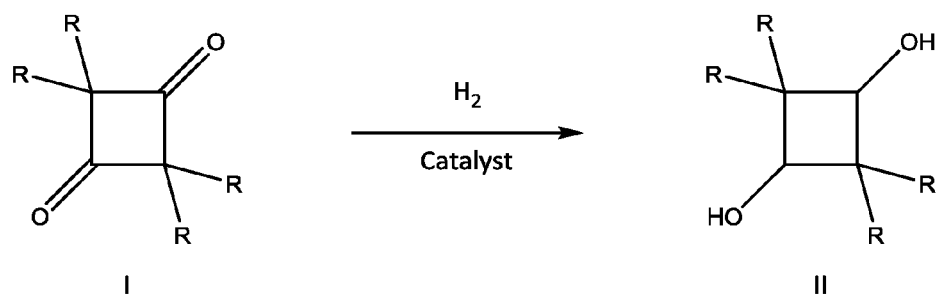

PROCESS FOR THE ISOMERIZATION OF 2,2,4,4-TETRAALKYLCYCLOBUTANE-1,3-DIOLS

FIELD OF THE INVENTION

This invention pertains to a process for the cis,trans-isomeration of cyclic diols. In particular, this invention pertains to a process for the cis,trans-isomerization of a 2,2,4,4-tetraalkylcyclobutane-1,3-diol in the presence of hydrogen and a catalyst comprising ruthenium deposited on a catalyst support material.

BACKGROUND OF THE INVENTION

Tetraalkylcyclobutane-1,3-diols can be important intermediates for producing a variety of polymeric materials which possess advantageous properties. For example, polyesters derived from dicarboxylic acids and 2,2,4,4-tetramethylcyclobutane-1,3-diol can possess higher glass transition temperatures, impact strength, weatherability, and hydrolytic stability in comparison to many other polyesters prepared from other commonly-used diols. Tetraalkylcyclobutane-1,3-diols can be prepared by the catalytic hydrogenation of the corresponding 2,2,4,4-tetraalkylcyclobutane-1,3-dione (I), as illustrated in FIG. 1 in which R is an alkyl group.

Typically, the hydrogenation of 2,2,4,4-tetraalkylcyclobutane-1,3-diones produces the corresponding 2,2,4,4-tetraalkylcyclobutane-1,3-diols as a mixture of cis and trans isomers. For example, U.S. Pat. No. 3,190,928 discloses the hydrogenation of 2,2,4,4-tetramethylcyclobutane-1,3-dione using nickel- or ruthenium-based catalysts to produce 2,2,4,4-tetraalkylcyclobutane-1,3-diols with molar cis:trans ratios that can vary widely from about 0.5 to about 1.2. Also, catalysts that produce the most desirable ratio of cis:trans isomers may not give the best yields or highest rates of hydrogenation. The cis:trans isomer ratio of 2,2,4,4-tetraalkylcyclobutane-1,3-diols can influence important properties such as, for example, the glass transition temperature, impact strength, and crystallization rate of the polyester polymers prepared from them. A cis:trans ratio that varies widely, in turn, can give polyesters with inconsistent and/or undesirable properties. A process to isomerize 2,2,4,4-tetraalkylcyclobutane-1,3-diols, therefore, would be desirable in order to produce 2,2,4,4-tetraalkylcyclobutane-1,3-diols with consistent cis:trans ratios regardless of the hydrogenation catalyst used. Such an isomerization process also would enable the efficient production of polyesters from 2,2,4,4-tetraalkylcyclobutane-1,3-diols with properties that can be tailored to a variety of applications.

SUMMARY OF THE INVENTION

We have found that the cis-trans ratio of 2,2,4,4-tetraalkylcyclobutane-1,3-diols may be modified by contacting the diol with a supported ruthenium catalyst in presence of hydrogen. A general embodiment of our invention, therefore, is a process for the isomerization of a 2,2,4,4-tetraalkylcyclobutane-1,3-diol, comprising contacting a starting 2,2,4,4-tetraalkylcyclobutane-1,3-diol having a molar ratio of cis to trans isomers of 0:1 to about 1.5:1 with hydrogen in the presence of a catalyst comprising about 0.1 to about 10 weight percent ruthenium, based on the total weight of the catalyst, deposited on a support material, to produce an isomerized 2,2,4,4-tetraalkylcyclobutane-1,3-diol having a different molar ratio of cis to trans isomers that the starting 2,2,4,4-tetraalkylcyclobutane-1,3-diol, in which the process has no net production of 2,2,4,4-tetraalkylcyclobutane-1,3-diol.

Our process may be used, in particular, for the isomerization of 2,2,4,4-tetramethylcyclobutane-1,3-diol, and can be carried out under modest pressures and temperatures using a supported ruthenium catalyst containing about 1 to about 9 weight percent ruthenium. Thus, another aspect of the invention is a process for the isomerization of a 2,2,4,4-tetraalkylcyclobutane-1,3-diol, comprising contacting trans-2,2,4,4-tetramethylcyclobutane-1,3-diol with a catalyst comprising about 1 to about 9 weight percent ruthenium, based on the total weight of the catalyst, deposited on a support comprising silica, alumina, silica-alumina, titania, zirconia, activated carbon, graphitized carbon, carbon nanotubes, zeolites, chromia, rare earth metal oxides, or mixtures thereof at a pressure of about 0.4 to about 3.5 megapascals and a temperature of about 100 to about 250° C. to form cis-2,2,4,4-tetramethylcyclobutane-1,3-diol, in which the process has no net production of 2,2,4,4-tetraalkylcyclobutane-1,3-diol.

The process of the invention also can be used to convert a 2,2,4,4-tetramethylcyclobutane-1,3-diol having a low trans isomer content to an isomerized 2,2,4,4-tetramethylcyclobutane-1,3-diol having a greater amount of trans isomer. Another embodiment of our invention, therefore, is a process for the isomerization of a 2,2,4,4-tetraalkylcyclobutane-1,3-diol, comprising contacting a starting 2,2,4,4-tetraalkylcyclobutane-1,3-diol having a molar ratio of cis to trans isomers of 3:1 to about 20:1 with hydrogen in the presence of a catalyst comprising about 0.1 to about 10 weight percent ruthenium, based on the total weight of the catalyst, deposited on a support, to produce an isomerized 2,2,4,4-tetraalkylcyclobutane-1,3-diol having a molar ratio of cis to trans isomers of about 1.5:1 to about 5:1, wherein the process has no net production of 2,2,4,4-tetraalkylcyclobutane-1,3-diol.

DESCRIPTION OF DRAWING

FIG. 1 represents the catalytic hydrogenation of a 2,2,4,4-tetraalkylcyclobutane-1,3-dione, in which R is an alkyl group (I) and the catalyst is comprised of ruthenium deposited on a catalyst support material, into its corresponding 2,2,4,4-tetraalkylcyclobutane-1,3-diol.

DETAILED DESCRIPTION

We have found that the isomerization of 2,2,4,4-tetraalkylcyclobutane-1,3-diols such as, for example, 2,2,4,4-tetramethylcyclobutane-1,3-diol, can be carried efficiently in the presence of a supported ruthenium catalyst and hydrogen. The process provided by the present invention comprises the isomerization of a 2,2,4,4-tetraalkylcyclobutane-1,3-diol by contacting a starting 2,2,4,4-tetraalkylcyclobutane-1,3-diol having a molar ratio of cis to trans isomers of 0:1 to about 1.5:1 with hydrogen in the presence of a catalyst comprising about 0.1 to about 10 weight percent ruthenium, based on the total weight of the catalyst, deposited on a support, to produce an isomerized 2,2,4,4-tetraalkylcyclobutane-1,3-diol having a different molar ratio of cis to trans isomers than the starting 2,2,4,4-tetraalkylcyclobutane-1,3-diol. Our process has no net production of 2,2,4,4-tetraalkylcyclobutane-1,3-diol. Our process can be used, for example, to isomerize a trans-tetraalkylcyclobutane-1,3-diol to a cis-tetraalkylcyclobutane-1,3-diol or vice versa. Our isomerization process can be operated independently of or in conjunction with the hydrogenation processes that are commonly used to prepare tetralkylcyclobutane-1,3-diols from the corresponding diones. The process of the invention thus enables the production of 2,2,4,4-tetraalkylcyclobutane-1,3-diols with an optimum cis-trans ratio regardless of the hydrogenation catalyst used.

Unless otherwise indicated, all numbers expressing quantities of ingredients, properties such as molecular weight, reaction conditions, and so forth used in the specification and claims are to be understood as being modified in all instances by the term "about." Unless indicated to the contrary, the numerical parameters set forth in the following specification and attached claims are approximations that may vary depending upon the desired properties sought to be obtained by the present invention. At the very least, each numerical parameter should be construed in light of the number of reported significant digits and by applying ordinary rounding techniques. Further, the ranges stated in this disclosure and the claims are intended to include the entire range specifically and not just the endpoint(s). For example, a range stated to be 0 to 10 is intended to disclose all whole numbers between 0 and 10 such as, for example 1, 2, 3, 4, etc., all fractional numbers between 0 and 10, for example 1.5, 2.3, 4.57, 6.1113, etc., and the endpoints 0 and 10. Also, a range associated with chemical substituent groups such as, for example, "C1 to C5 hydrocarbons", is intended to specifically include and disclose C1 and C5 hydrocarbons as well as C2, C3, and C4 hydrocarbons.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in its respective testing measurements.

Also, it is to be understood that the mention of one or more process steps does not preclude the presence of additional process steps before or after the combined recited steps or intervening process steps between those steps expressly identified. Moreover, the lettering of process steps or ingredients is a convenient means for identifying discrete activities or ingredients and the recited lettering can be arranged in any sequence, unless otherwise indicated.

As used herein, the terms "tetraalkylcyclobutanediol" and "tetramethylcyclobutanediol" are understood to be synonymous with the terms "2,2,4,4-tetraalkylcyclobutane-1,3-diol" and "2,2,4,4-tetramethylcyclobutane-1,3-diol" respectively. The term "starting 2,2,4,4-tetraalkylcyclobutane-1,3-diol" or "starting 2,2,4,4-tetramethylcyclobutane-1,3-diol" is intended to mean a 2,2,4,4-tetraalkylcyclobutane-1,3-diol or 2,2,4,4-tetramethylcyclobutane-1,3-diol that is used as a reactant in the process of the invention, i.e., a tetraalkylcyclobutanediol or 2,2,4,4-tetramethylcyclobutane-1,3-diol that has not been isomerized by the process of the invention. By contrast, the term "isomerized 2,2,4,4-tetraalkylcyclobutane-1,3-diol" or "isomerized 2,2,4,4-tetramethylcyclobutane-1,3-diol," as used herein, is understood to mean a 2,2,4,4-tetraalkylcyclobutane-1,3-diol or 2,2,4,4-tetramethylcyclobutane-1,3-diol that has been subjected to and isomerized by the process of the invention.

Our process provides a process for isomerizing a 2,2,4,4-tetraalkylcyclobutane-1,3-diol having the formula (II):

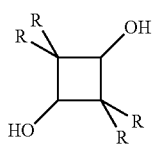

II wherein the R groups are identical, alkyl radicals having 1 to 8 carbon atoms. For example, the alkyl radicals represented by R can comprise 1 to 6 carbon atoms, 1 to 4 carbon atoms, or 1 to 2 carbon atoms. The alkyl radicals may be linear or branched. Representative alkyl groups include, but are not limited to, methyl, ethyl, propyl, isopropyl, butyl, isobutyl, pentyl, hexyl, heptyl, and octyl. Some examples of 2,2,4,4-tetralkylcyclobutane-1,3-diols that can be used in the process of the invention include 2,2,4,4-tetramethylcyclobutane-1,3-diol, 2,2,4,4-tetraethylcyclobutane-1,3-diol, 2,2,4,4-tetra-n-propylcyclobutane-1,3-diol, 2,2,4,4-tetra-n-butylcyclobutane-1,3-diol, 2,2,4,4-tetra-n-amylcyclobutane-1,3-diol, 2,2,4,4-tetraisobutylcyclobutane-1,3-diol, 2,2,4,4-tetra-n-hexylcyclobutane-1,3-diol, 2,2,4,4-tetra-n-heptylcyclobutane-1,3-diol, and 2,2,4,4-tetra-n-octylcyclobutane-1,3-diol. Our invention can be further described and illustrated herein with particular reference to 2,2,4,4-tetramethylcyclobutane-1,3-diol in which R is a methyl radical. It is understood that the embodiments described for 2,2,4,4-tetramethylcyclobutane-1,3-diol also apply to the other 2,2,4,4-tetraalkylcyclobutane-1,3-diols described hereinabove.

Tetraalkylcyclobutanediols typically are produced by hydrogenation of the corresponding tetraalkylcyclobutanediones using a variety of metal catalysts such as, for example, those catalysts containing nickel, ruthenium, and cobalt. For example, the hydrogenation of 2,2,4,4-tetramethylcyclobutane-1,3-dione to 2,2,4,4-tetramethylcyclobutane-1,3-diol can be carried out using nickel- or ruthenium-containing catalysts as described in U.S. Pat. Nos. 3,000,906, 3,190,928; 5,169,994; 5,258,556; and 2,936,324. Cobalt-containing catalysts also may be used. For example, U.S. Pat. Nos. 5,528,556 and 5,169,994 disclose the use of Raney cobalt for hydrogenation of 2,2,4,4-tetramethylcyclobutane-1,3-dione to 2,2,4,4-tetramethylcyclobutane-1,3-diol. In one embodiment of our process, for example, the starting 2,2,4,4-tetraalkylcyclobutane-1,3-diol is produced by hydrogenation of 2,2,4,4-tetramethylcyclobutane-1,3-dione.

The starting tetralkylcyclobutanediol can be used as a mixture of cis and trans isomers or as purified cis or trans isomers. For example, 2,2,4,4-tetramethylcyclobutane-1,3-diol may be used as pure cis or trans isomers, or as a mixture of cis and trans isomers. In one embodiment of our invention, the starting 2,2,4,4-tetraalkylcyclobutane-1,3-diol can have a cis:trans molar ratio of about 0:1 to about 1.5:1. Persons of skill in the art will understand that a cis:trans ratio of 0:1 is the equivalent of having the pure trans isomer. Some other representative examples of ranges of cis:trans ratios of the starting 2,2,4,4-tetraalkylcyclobutane-1,3-diol are 0.2:1 to about 0.4:1, about 0.2:1 to about 0.7:1, about 0.2:1 to about 1:1, and about 0.2:1 to about 1.2:1. In one example, the starting 2,2,4,4-tetraalkylcyclobutane-1,3-diol can comprise a substantially pure trans-2,2,4,4-tetraalkylcyclobutane-1,3-diol, that is, a 2,2,4,4-tetraalkylcyclobutane-1,3-diol comprising about 95 mole percent or greater of the trans isomer.

The starting 2,2,4,4-tetraalkylcyclobutane-1,3-diol is contacted with hydrogen in the presence of a supported ruthenium catalyst. The source and purity of the hydrogen gas are not critical, and the hydrogen gas may comprise fresh hydrogen or a mixture of fresh hydrogen and recycled hydrogen. For example, hydrogen can be a mixture of hydrogen, optionally minor amounts, typically less than about 30 mole %, of components such as CO and $CO_2$, and inert gases, such as argon, nitrogen, or methane. Typically, the hydrogen gas comprises at least about 70 mole % of hydrogen. For example, the hydrogen gas can comprise at least 90 mole % or, in another example, at least 97 mole %, of hydrogen. The hydrogen gas can be obtained from any of the conventional sources well known in the art such as, for example, by partial oxidation or steam reforming of natural gas. Pressure swing absorption can be used if a high purity hydrogen gas is desired. If hydrogen gas recycle is utilized in the isomerization process, then the recycled hydrogen gas may contain minor amounts of one or more products of the isomerization reaction which have not been fully condensed in the product recovery stage downstream from the isomerization reaction.

The temperature and hydrogen pressure used in the isomerization process of the invention can also be varied over a wide range depending on the activity of the catalyst, the mode of operation, and the desired rate of conversion. Typically, the process can be carried out under elevated hydrogen pressures of up to about 50.66 MPa (megapascals) and at temperatures of about 75° C. to about 250° C. Some additional, more specific ranges of hydrogen pressures are about 0.3 to about 35 MPa, about 0.3 to about 5.2 MPa, about 0.3 to about 3.5 MPa, and about 0.4 to about 2.8 MPa. Some additional temperature ranges for the isomerization reaction are about 100 to about 200° C. and about 100 to about 175° C. Persons of having ordinary skill in the art will recognize that any combination of the above temperatures and pressures can be used. In one embodiment of the invention, for example, the isomerization process can be carried at a temperature of about 100 to about 200° C. and a hydrogen pressure of about 0.4 to about 2.8 megapascals.

The catalyst of the present invention comprises ruthenium deposited on a catalyst support. The term "support," as used in the context of the present specification and claims is intended to have its commonly accepted meaning as would be well-understood by persons of ordinary skill in the art, that is, a nominally inert material on which a catalytically active material, e.g., typically a metal, is deposited. The term, "deposited on," as used herein, is understood to mean any known method for adding the metal to the support including, but not limited to, depositing, adsorption, impregnation, ion-exchange, admixing, coprecipitation, and the like.

The ruthenium may be deposited on any recognized support material. For example, the support may comprise materials such as chromia, rare earth metal oxides, mixed metal oxides, zinc oxide, alumina, silica, silica-alumina, silicon carbide, zirconia, titania, activated carbon, graphite, graphitized carbon, carbon nano-tubes, zeolites, or mixtures thereof. These support materials are well-known to persons skilled in the art. For example, graphitized carbon supports are described in Rossetti et al. *Catalysis Today*, 2005, 102-103, pp. 219-224, and in U.S. Pat. No. 7,115,239. The catalyst support may be further compounded with one or more binders to aid in pellet formation. The catalyst support along with any binder can be fabricated in any of the commonly used forms well-known in the art such as, for example, powders, extrudates, chips, granules, monoliths, pellets, cylinders, rings, saddles, spheres, stars, single lobe or multiple-lobe shapes, and the like. Depending on the particular support material employed and/or the method used to prepare a catalyst, ruthenium may be deposited primarily on the surface of the support or distributed throughout the support.

In one embodiment, the catalyst comprises ruthenium supported on carbon nanotubes. Carbon nanotubes (also known as fibrils) are well-known in the art as vermicular carbon deposits having diameters less than 1.0 μm. Some additional examples of carbon nanotube diameters are less than 0.5 μm and less than 0.2 μm. Carbon nanotubes can be either multi walled (i.e., have more than one graphene layer more or less parallel to the nanotube axis) or single walled (i.e., have only a single graphene layer parallel to the nanotube axis). Other types of carbon nanotubes are also known, such as fishbone fibrils (e.g., wherein the graphene sheets are disposed in a herringbone pattern with respect to the nanotube axis), etc. As produced, carbon nanotubes may be in the form of discrete nanotubes, aggregates of nanotubes (i.e., dense, microscopic particulate structures comprising entangled carbon nanotubes) or a mixture of both. Some representative examples of carbon nanotubes are described in U.S. Patent Application Publication No.'s 2009 0208391; 2008 0176069; 2008 0175787; 2006 0239893; 2006 0142149; 2006 0142148; and 2003 0039604.

The catalyst can have a wide range of ruthenium content. Typically, the total amount of ruthenium present may be about 0.1 to about 10 weight percent based on the total weight of the catalyst. Some additional examples of ruthenium content are about 0.1 to about 9 weight percent, and about 0.2 to about 7 weight percent. For example, the catalyst can comprise about 1 to about 9 weight percent ruthenium deposited on a support comprising activated carbon, carbon nanotubes, silica, alumina, or a mixture thereof.

The catalyst may be prepared by conventional techniques such as, for example, vapor deposition or impregnation of ruthenium onto the support material. Ruthenium may be provided as the metal itself or in the form of well-known ruthenium compounds such as, for example, ruthenium salts of inorganic or organic acids, ruthenium oxides, and organometallic complexes containing ruthenium. The support material may be impregnated with ruthenium metal by immersing the support material in a solution of a ruthenium compound in a suitable solvent or by spraying the support material with the solution. The support material typically is dried and the catalyst exposed to a reducing environment, e.g., hydrogen, in order to reduce the ruthenium compounds to ruthenium metal.

Our isomerization process produces an isomerized 2,2,4,4-tetraalkylcyclobutane-1,3-diol having a different ratio of cis to trans isomers than the starting 2,2,4,4-tetraalkylcyclobutane-1,3-diol. For example, the starting tetraalkylcyclobutanediol can have a cis:trans isomer ratio of about 0:1 to about 1.5:1 and the isomerized tetraalkylcyclobutanediol can have a cis:trans molar ratio of greater than 1:1 to about 2:1. In another example, the starting tetraalkylcyclobutanediol can be 2,2,4,4-tetramethylcyclobutane-1,3-diol having a cis:trans isomer ratio of about 0:1 to less than 1:1 and produces an isomerized 2,2,4,4-tetramethylcyclobutane-1,3-diol with a cis:trans molar ratio of greater than 1:1 to about 2:1. In yet another example, the starting tetraalkylcyclobutanediol is a trans-2,2,4,4-tetramethylcyclobutane-1,3-diol (cis:trans ratio of 0) and produces an isomerized 2,2,4,4-tetramethylcyclobutane-1,3-diol with a cis:trans ratio of about 0.3:1 to about 1.5:1. In yet another example, the starting tetraalkylcyclobutanediol is a 2,2,4,4-tetramethylcyclobutane-1,3-diol having a cis:trans ratio of about 0.1:1 to about 1:1 that produces an isomerized 2,2,4,4-tetramethylcyclobutane-1,3-diol having a cis:trans ratio of about 0.4:1 to about 1.5:1. Our process also can be used to isomerize cis-tetraalkylcyclobutanediols to the trans isomers. For example, the starting tetraalkylcyclobutanediol can have a cis:trans isomer ratio of about 3:1 to about 20:1 to produce an isomerized tetraalkylcyclobutanediol having a cis:trans ratio of about 1.5:1 to about 5:1.

The process of the invention has no net production of 2,2,4,4-tetraalkylcyclobutane-1,3-diol. The phrase "no net production" is intended to mean that no 2,2,4,4-tetraalkylcyclobutane-1,3-diol in addition to that already present as the starting 2,2,4,4-tetraalkylcyclobutane-1,3-diol is generated over the course of the isomerization reaction. For example, 1 mole of a starting tetraalkylcyclobutanediol would be expected to produce about 1 mole or less (as a result of adventitious losses from handling, transfers, by-product formation, etc.) of isomerized tetraalkylcyclobutanediol. The present invention, therefore, would be distinguished from a process for the preparation of a tetraalkylcyclobutanediol by hydrogenation of the corresponding tetraalkylcyclobutanedione because there would be a net increase in the amount of tetraalkylcyclobutanediol over the course of the hydrogenation process.

The isomerization process may be carried out using the neat tetraalkylcyclobutanediol or in the presence of a solvent that may be selected from a wide variety of compounds or mixture of compounds. The solvent can be any substance that is liquid under the operating conditions of the isomerization process, does not adversely affect the isomerization process, and is substantially inert or shows limited reactivity (e.g., typically less than 1% conversion under process conditions) with respect to the catalyst, hydrogen and tetraalkylcyclobutanediol. Some representative examples of solvents that may be used to dissolve the starting 2,2,4,4-tetraalkylcyclobutane-1,3-diol, include water, alcohols, ethers, glycols, glycol ethers, alkanes, esters, and mixtures thereof. Some specific examples of solvents that may used in the isomerization process include, but are not limited to, water, methanol, ethanol, propanol, 1-butanol, 2-butanol, 2-ethylhexanol, 2,2-dimethyl-1,3-propanediol, ethylene glycol, propylene glycol, 1,4-butanediol, diethylene glycol, hexane, heptane, cyclohexane, octane, decane, diethyl ether, diisopropyl ether, tetrahydrofuran, methyl tert-butyl ether, ethylene glycol monobutyl ether, diethylene glycol monobutyl ether, ethyl acetate, n-propyl acetate, isopropyl isobutyrate, isobutyl propionate, octyl acetate, isobutyl isobutyrate, isobutyl acetate, methyl butyrate, and mixtures thereof. In one embodiment, for example, the solvent comprises isobutyl isobutyrate. Typically, the 2,2,4,4-tetraalkylcyclobutane-1,3-diol can be dissolved in the solvent at a concentration of about 1 to about 60 weight percent, based on the total weight of the tetraalkylcyclobutanediol solution. Some other examples of tetraalkylcyclobutanediol concentrations are about 5 to about 50 weight percent and about 10 to about 25 weight percent. In another example, the tetraalkylcyclobutanediol comprises trans-2,2,4,4-tetraalkylcyclobutanediol and is dissolved in a solvent comprising isobutyl isobutyrate at a concentration of about 1 to about 60 weight percent, about 5 to about 50 weight percent, or about 10 to about 25 weight percent.

The isomerization process can be carried out as a batch, semi-continuous or continuous process, and may utilize a variety of reactor types. Some examples of suitable reactor types include stirred tank, continuous stirred tank, slurry, tubular, fixed bed, and trickle bed. The term "continuous," as used herein, means a process wherein reactants are introduced and products withdrawn simultaneously in an uninterrupted manner. By "continuous" it is meant that the process is substantially or completely continuous in operation in contrast to a "batch" process. The term "batch" process as used herein means a process wherein all the reactants are added to the reactor and then processed according to a predetermined course of reaction during which no material is fed or removed into the reactor. For example, in a batch operation, a slurry of the catalyst in the tetraalkylcyclobutanediol and/or a solvent in which the tetraalkylcyclobutanediol has been dissolved is fed to a pressure vessel equipped with means for agitation. The pressure vessel is then pressurized with hydrogen to a predetermined pressure followed by heating the reaction mixture to the desired temperature. After the reaction is complete, the reaction mixture is removed from the pressure vessel, the catalyst is separated by filtration, and the isomerized tetraalkylcyclobutanediol is isolated, for example, by distillation or by crystallization. The term "semicontinuous" means a process in which some of the reactants are charged at the beginning of the process and the remaining reactants are fed continuously as the reaction progresses. Alternatively, a semi-continuous process also may include a process similar to a batch process in which all the reactants are added at the beginning of the process except that one or more of the products are removed continuously as the reaction progresses.

For economic and operability reasons, the process is advantageously operated as a continuous process. Continuous operation may utilize a fixed bed with a larger particle size of catalyst such as, for example, granules, pellets, various multilobal shaped pellets, rings, or saddles that are well known to skilled persons in the art. As an example of a continuous process, a high pressure, tubular or columnar reactor utilizing a fixed catalyst bed may be used in which the liquid tetraalkylcyclobutanediol, with or without a solvent, can be fed continuously into the top of the bed at elevated pressure and temperature. The crude isomerization product can be removed from the base of the reactor. Alternatively, it is possible to feed the tetraalkylcyclobutanediol into the bottom of the bed and remove the isomerized product from the top of the reactor. It is also possible to use 2 or more catalyst beds connected in parallel or in series to improve conversion, to reduce the quantity of catalyst, or to bypass a catalyst bed for periodic maintenance or catalyst removal. Another mode of continuous operation utilizes a slurry of the catalyst in an agitated pressure vessel that is equipped with a filter leg to permit continuous removal of a solution of the isomerized product in the tetraalkylcyclobutanediol and/or a solvent. In this manner a liquid, starting tetraalkylcyclobutanediol or solution thereof can be continuously fed to and the product or product solution continuously removed from an agitated pressure vessel containing a slurry of the catalyst.

In one embodiment, for example, a starting 2,2,4,4-tetramethylcyclobutane-1,3-diol, a solvent, and hydrogen can be contacted continuously with a catalyst comprising ruthenium deposited on a support material in an isomerization zone at a hydrogen pressure of about 0.7 MPa to about 6.9 MPa and a temperature of about 75 to about 250° C. This embodiment can include continuously recovering an effluent from the isomerization zone comprising the solvent and an isomerized 2,2,4,4-tetramethylcyclobutane-1,3-diol having a cis:trans ratio different from that of the starting 2,2,4,4-tetramethylcyclobutane-1,3-diol. In another embodiment, the process may further comprise continuously recycling a portion of the product effluent to the isomerization zone. The isomerization zone may be any suitable reactor type including, but are not limited to, stirred tank, continuous stirred tank, slurry, tubular, fixed bed, and trickle bed. For example, the process of the invention may be carried out in a trickle bed reactor operated in the liquid phase.

The process may be conducted in the liquid phase, the vapor phase, or a combination of liquid and vapor phases. For example, the process may be carried in the vapor phase in a similar manner as the hydrogenation processes disclosed in U.S. Pat. No. 5,395,987. As a vapor phase process, our isomerization process can be operated using vaporous feed conditions by feeding the tetraalkylcyclobutanediol in essentially liquid free, vaporous form to an isomerization zone comprising the supported ruthenium catalyst. Hence, the feed stream is introduced into the isomerization zone at a temperature which is above the dew point of the mixture. The term "dew point", as used herein, means that temperature at which a gas or a mixture of gases is saturated with respect to a condensable component. Typically, the feed temperature of the vaporous feed mixture to the isomerization zone is from about 5° C. to about 10° C. or more above its dew point at the operating pressure.

A convenient method of forming a vaporous mixture is to spray liquid tetraalkylcyclobutanediol or a tetraalkylcyclobutanediol solution into a stream of hot hydrogen-containing gas to form a saturated or partially saturated vaporous mixture. Alternatively, such a vapor mixture can be obtained by bubbling a hot hydrogen-containing gas through a body of the liquid tetraalkylcyclobutanediol or tetraalkylcyclobutanediol solution. If a saturated vapor mixture is formed it should then be heated further or diluted with more hot gas to produce a partially saturated vaporous mixture prior to contact with the catalyst. To maintain the vaporous feed stream above its dew point at the inlet end of a catalyst bed at the operating pressure, the hydrogen-containing gas: tetraalkylcyclobutanediol molar ratio is desirably about 10:1 to about 8000:1 or, in another example, about 200:1 to about 1000:1.

The process of the invention can be used to isomerize trans-2,2,4,4-tetramethylcyclobutane-1,3-diol to a cis-2,2,4,4-tetramethylcyclobutane-1,3-diol or a mixture of cis- and trans-2,2,4,4-tetramethylcyclobutane-1,3-diols. Thus, another aspect of our invention is process for the isomerization of a 2,2,4,4-tetraalkylcyclobutane-1,3-diol, comprising contacting trans-2,2,4,4-tetramethylcyclobutane-1,3-diol with a catalyst comprising about 1 to about 9 weight percent ruthenium, based on the total weight of the catalyst, deposited on a support comprising silica, alumina, silica-alumina, titania, zirconia, activated carbon, graphitized carbon, carbon nanotubes, zeolites, chromia, rare earth metal oxides, or mixtures thereof at a pressure of about 0.4 to about 3.5 megapascals and a temperature of about 100 to about 250° C. to form cis-2,2,4,4-tetramethylcyclobutane-1,3-diol, wherein the process has no net production of 2,2,4,4-tetraalkylcyclobutane-1,3-diol. It is understood that the above process encompasses the various embodiments of the cis:trans isomer ratios, catalyst support, reaction conditions of temperature and pressure, reactor formats, catalyst loadings, and solvents described hereinabove.

For example, the trans-2,2,4,4-tetramethylcyclobutane-1,3-diol can be dissolved in at least one solvent selected from water, alcohols, ethers, glycols, glycol ethers, alkanes, and esters. Some specific examples of solvents include water, methanol, ethanol, propanol, 1-butanol, 2-butanol, 2-ethylhexanol, 2,2-dimethyl-1,3-propanediol, ethylene glycol, propylene glycol, 1,4-butanediol, diethylene glycol, hexane, heptane, cyclohexane, octane, decane, diethyl ether, diisopropyl ether, tetrahydrofuran, methyl tert-butyl ether, ethylene glycol monobutyl ether, diethylene glycol monobutyl ether, ethyl acetate, n-propyl acetate, isopropyl isobutyrate, isobutyl propionate, octyl acetate, isobutyl isobutyrate, methyl butyrate, isobutyl acetate, and mixtures thereof. In another example, the support can comprise alumina, activated carbon, graphitized carbon, silica, silica-alumina, or carbon nanotubes.

The process of the invention also can be used to isomerize a 2,2,4,4-tetraalkylcyclobutane-1,3-diol having a high cis:trans ratios. Another embodiment of our invention, therefore, is a process for the isomerization of a 2,2,4,4-tetraalkylcyclobutane-1,3-diol, comprising contacting a starting 2,2,4,4-tetraalkylcyclobutane-1,3-diol having a molar ratio of cis to trans isomers of 3:1 to about 20:1 with hydrogen in the presence of a catalyst comprising about 0.1 to about 10 weight percent ruthenium, based on the total weight of the catalyst, deposited on a support, to produce an isomerized 2,2,4,4-tetraalkylcyclobutane-1,3-diol having a ratio of cis to trans isomers of about 1.5:1 to about 5:1, wherein the process has no net production of 2,2,4,4-tetraalkylcyclobutane-1,3-diol. It will be apparent to persons skilled in the art that the above process encompasses the various embodiments of the cis: trans isomer ratios, catalyst support, reaction conditions of temperature and pressure, reactor formats, catalyst loadings, and solvents that have been described previously. For example, the above process can be in operated as a continuous process and can employ a solvent to dissolve the starting tetramethylcyclobutanediol. As noted above, the solvent can include one or more of water, methanol, ethanol, propanol, 1-butanol, 2-butanol, 2-ethylhexanol, 2,2-dimethyl-1,3-propanediol, ethylene glycol, propylene glycol, 1,4-butanediol, diethylene glycol, hexane, heptane, cyclohexane, octane, decane, diethyl ether, diisopropyl ether, tetrahydrofuran, methyl tert-butyl ether, ethylene glycol monobutyl ether, diethylene glycol monobutyl ether, ethyl acetate, n-propyl acetate, isopropyl isobutyrate, isobutyl propionate, octyl acetate, isobutyl isobutyrate, isobutyl acetate methyl butyrate, or mixtures thereof at a concentration of about 10 to about 25 weight percent, based on the total weight of the solution.

The invention also includes the following embodiments that are set forth below. Embodiment A is a process for the isomerization of a 2,2,4,4-tetraalkylcyclobutane-1,3-diol, comprising contacting a starting 2,2,4,4-tetraalkylcyclobutane-1,3-diol having a ratio of cis to trans isomers of about 0:1 to about 1.5:1 with hydrogen in the presence of a catalyst comprising about 0.1 to about 10 weight percent ruthenium, based on the total weight of the catalyst, deposited on a support, to produce an isomerized 2,2,4,4-tetraalkylcyclobutane-1,3-diol having a different ratio of cis to trans isomers than the starting 2,2,4,4-tetraalkylcyclobutane-1,3-diol, in which the process has no net production of 2,2,4,4-tetraalkylcyclobutane-1,3-diol.

The process of Embodiment A wherein the starting 2,2,4,4-tetraalkylcyclobutane-1,3-diol has the general formula (II):

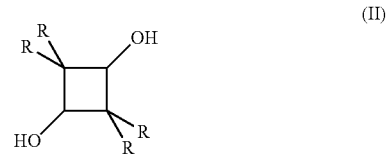

wherein R is methyl, ethyl, propyl, butyl, pentyl, hexyl, heptyl, or octyl; and the support comprises silica, alumina, silica-alumina, titania, zirconia, activated carbon, graphite, graphitized carbon, carbon nanotubes, zeolites, chromia, rare earth metal oxides, or mixtures thereof.

The process of Embodiment A or Embodiment A with any of the intervening features wherein R is methyl.

The process of Embodiment A or Embodiment A with any of the intervening features wherein the starting 2,2,4,4-tetraalkylcyclobutane-1,3-diol has a cis:trans molar ratio of about 0:1 to less than 1:1 and the isomerized 2,2,4,4-tetraalkylcyclobutane-1,3-diol has a cis:trans molar ratio of greater than 1:1 to about 2:1.

The process of Embodiment A or Embodiment A with any of the intervening features wherein the catalyst comprises about 1 to about 9 weight percent ruthenium and the support comprises activated carbon, graphitized carbon, carbon nanotubes, silica, alumina, or a mixture thereof.

The process of Embodiment A or Embodiment A with any of the intervening features which is at a temperature of about 100 to about 200° C. and a hydrogen pressure of about 0.4 to about 2.8 megapascals.

The process of Embodiment A or Embodiment A with any of the intervening features wherein the starting 2,2,4,4-tetraalkylcyclobutane-1,3-diol is dissolved in at least one solvent selected from water, alcohols, ethers, glycols, glycol ethers, alkanes, and esters.

The process of Embodiment A or Embodiment A with any of the intervening features wherein the solvent is selected from water, methanol, ethanol, propanol, 1-butanol, 2-butanol, 2-ethylhexanol, 2,2-dimethyl-1,3-propanediol, ethylene glycol, propylene glycol, 1,4-butanediol, diethylene glycol, hexane, heptane, cyclohexane, octane, decane, diethyl ether, diisopropyl ether, tetrahydrofuran, methyl tert-butyl ether, ethylene glycol monobutyl ether, diethylene glycol monobutyl ether, ethyl acetate, n-propyl acetate, isopropyl isobutyrate, isobutyl propionate, octyl acetate, isobutyl isobutyrate, isobutyl acetate, methyl butyrate, and mixtures thereof.

The process of Embodiment A or Embodiment A with any of the intervening features which is a continuous process.

The process of Embodiment A or Embodiment A with any of the intervening features wherein the process is conducted in the liquid phase, vapor phase, or a combination of liquid and vapor phase.

The process of Embodiment A or Embodiment A with any of the intervening features wherein the starting 2,2,4,4-tetraalkylcyclobutane-1,3-diol is produced by hydrogenation of 2,2,4,4-tetramethylcyclobutane-1,3-dione.

The process of the invention are further described and illustrated by the following examples.

EXAMPLES

The invention is further illustrated by the following examples. All percentages are by weight unless specified otherwise. The carbon nanotube support material used in the examples was 1.6 mm (1/16 inch) extrudates obtained from Hyperion Catalyst International, Inc. Catalyst surface areas were measured volumetrically using the Brunauer-Emmett-Teller (BET) method. Analysis of reaction products was performed by gas chromatography using a DB™-Wax column (30 meters×0.25 mm ID, 0.5 micron film thickness) over a temperature range of 50 to 240° C. and a flame ionization detector. The reaction samples were dissolved in dimethyl sulfoxide before injection into the gas chromatograph. Trace amounts (e.g., typically less than 0.1 weight percent) of 2,2,4-trimethyl-1,3-pentanediol, 2,4-dimethyl-3-pentanol (diisopropyl carbinol), 2,2,4-trimethyl-3-pentanol, 2,2,4-trimethyl-1-pentanol, 2,2,4-trimethyl-3-oxo-1-pentanol, and 2,2,4,4-cyclobutaneketol also were detected by GC in the Examples unless indicated otherwise. All pressures are reported as gauge unless indicated otherwise.

Example 1

A pre-reduced catalyst (2 g) containing 7 weight percent Ru on a graphitized carbon support (purchased from BASF Catalysts under the designation "C3610") and having a surface area of 589 m$^2$/g was loaded in a 100 mL stainless steel autoclave with 6 g of trans-2,2,4,4-tetramethylcyclobutane-1,3-diol and 54 g of isobutyl isobutyrate (IBIB). The autoclave was agitated and purged twice with 0.7 MPa (100 psig) helium at ambient temperature and then purged with 0.7 MPa (100 psig) hydrogen. The autoclave was heated to 100° C. and pressurized to 1.4 MPa (200 psig) with hydrogen. After 2 hours, a product sample was taken and analyzed by gas chromatograph (GC). The conversion of trans-2,2,4,4-tetramethylcyclobutane-1,3-diol was 55% and the ratio of cis to trans isomers was 1.2:1.

Example 2

The same catalyst in Example 1 (0.9 g) was loaded in a 100 mL stainless steel autoclave reactor with 7 g of trans-2,2,4,4-tetramethylcyclobutane-1,3-diol and 63 g of isobutyl isobutyrate. The autoclave was agitated and purged twice with helium (0.7 MPa, 100 psig) at ambient temperature and then purged with hydrogen (0.7 MPa, 100 psig). The autoclave was heated to 120° C. and pressurized to 1.4 MPa (200 psig) with hydrogen. After 3 hours, a product sample was taken and analyzed. The conversion of trans-2,2,4,4-tetramethylcyclobutane-1,3-diol was 46% and the ratio of cis to trans isomers was 0.85:1.

Example 3

A mixture of 6 g of trans-2,2,4,4-tetramethylcyclobutane-1,3-diol, 54 g of IBIB, and 2 grams of a 2 weight percent Ru on silica catalyst (surface area=300 m$^2$/g, obtained from BASF Catalysts) was loaded in a 100 mL stainless steel autoclave reactor. The autoclave was agitated and purged twice with helium (0.7 MPa, 100 psig) at an ambient temperature and purged with hydrogen at a pressure of 0.7 MPa (100 psig). The autoclave was then heated to 110° C. and pressurized to 1.4 MPa (200 psig) with hydrogen. After 2 hours, a product sample was taken and analyzed by GC. The conversion of trans-2,2,4,4-tetramethylcyclobutane-1,3-diol was 32% and the ratio of cis to trans isomers was 0.47:1.

Example 4

A mixture of 6 g of trans-2,2,4,4-tetramethylcyclobutane-1,3-diol, 54 g of IBIB, and 2 grams of a 2 weight percent Ru on a-alumina catalyst (surface area=40 m$^2$/g, obtained from BASF Catalysts) was loaded in a 100 mL stainless steel autoclave. The autoclave was agitated and purged twice with helium at a pressure of 0.7 MPa (100 psig) at ambient temperature and with hydrogen at a pressure of 0.7 MPa (100 psig). The autoclave was then heated to 110° C. and pressurized to 1.4 MPa (200 psig) with hydrogen. After 2 hours, a product sample was taken and analyzed by GC. The conversion of trans-2,2,4,4-tetramethylcyclobutane-1,3-diol was 35% and the ratio of cis to trans isomers was 0.55:1.

Example 5

The same catalyst in Example 1 (0.9 g) was loaded in a 100 mL stainless steel autoclave reactor with 7 g of trans-2,2,4,4-tetramethylcyclobutane-1,3-diol and 63 g of IBIB. The autoclave was agitated and purged twice with helium at a pressure of 0.7 MPa (100 psig) at ambient temperature and with hydrogen at a pressure of 0.7 MPa (100 psig). The autoclave was heated to 120° C. and pressurized to 2.1 MPa (300 psig) with hydrogen. After 4 hours, a product sample was taken and analyzed by GC. The conversion of trans-2,2,4,4-tetramethylcyclobutane-1,3-diol was 54% and the ratio of cis to trans isomers was 1.16:1.

Comparative Example 1

Isomerization in the Absence of Hydrogen and Catalyst

Trans-2,2,4,4-tetramethylcyclobutane-1,3-diol (6 g) and 54 g of isobutyl isobutyrate were added to a 100 mL stainless steel autoclave reactor. The autoclave was agitated and purged twice with helium a pressure of 0.7 MPa (100 psig) at ambient temperature. The autoclave was then heated to 150° C. After 4 hours, a product sample was taken and analyzed by GC. The conversion of trans-2,2,4,4-tetramethylcyclobutane-1,3-diol was 1.6% and the ratio of cis to trans isomers was 0.016:1.

Comparative Example 2

A mixture of 65 g IBIB and 2 g of 5 weight percent Pd on alumina powder (surface area=88 $m^2/g$, obtained from Engelhard, now BASF Catalysts) was loaded in a 100 mL stainless steel autoclave. The autoclave was agitated and purged twice with helium (0.7 MPa, 100 psig) and then hydrogen at pressure of 0.7 MPa (100 psig) at ambient temperature. The autoclave was heated to 150° C. and the reactor pressure was increased to 2.8 MPa (400 psig) with hydrogen. After the 1 hour catalyst reduction, the reactor was cooled to approximately 50° C. and 3.5 g of trans-2,2,4,4-tetramethylcyclobutane-1,3-diol was added to the autoclave. The autoclave was agitated and purged twice with helium (0.7 MPa, 100 psig) followed by hydrogen (0.7 MPa, 100 psig). The autoclave was then heated to 200° C. and pressurized to 2.8 MPa (400 psig). After 3 hours, GC analysis of the reaction mixture show the cis- and trans-2,2,4,4-tetramethylcyclobutane-1,3-diol concentrations to be 0.042 and 5.24 weight percent, respectively. Because the conversion to the cis isomer was low, the concentration of the trans-2,2,4,4-tetramethylcyclobutane-1,3-diol isomer in the product mixture was higher than in the starting mixture, presumably as the result of an error in the GC analysis. The conversion of the trans-isomer was 0.84% and the ratio of the cis to trans isomers was 0.008. This conversion was based on the ratio of the cis isomer to the total amount of 2,2,4,4-tetramethylcyclobutane-1,3-diol in the product mixture.

Comparative Example 3

A 5 weight percent Pt on activated carbon powder catalyst (2.97 g, surface area=607 $m^2/g$, obtained from Engelhard, now BASF Catalysts) was dried overnight in a conventional oven at 105° C. and charged to a 100 mL stainless steel autoclave. The autoclave was purged twice with helium (0.7 MPa, 100 psig) and then hydrogen (0.7 MPa, 100 psig) at ambient temperature. The autoclave was heated to 150° C. and the reactor pressure was increased to 2.8 MPa (400 psig) with hydrogen. After the 1 hour, the autoclave was cooled to approximately 50° C. and 66.5 g of isobutyl isobutyrate (IBIB) and 3.5 g of trans-2,2,4,4-tetramethylcyclobutane-1,3-diol were added. The autoclave was agitated and purged twice with helium (0.7 MPa, 100 psig) followed by hydrogen (0.7 MPa, 100 psig). The autoclave was then heated to 200° C. and pressurized to 2.8 MPa (400 psig). After 3 hours, GC analysis of the reaction mixture show the cis- and trans-2,2,4,4-tetramethylcyclobutane-1,3-diol concentrations to be 0.043 and 3.93 weight percent, respectively. The conversion of the trans-diol was 21% and the ratio of cis to trans isomers was 0.01. Significant amount of by-products such as 2,2,4-trimethyl-1,3-pentanediol, 2,4-dimethyl-3-pentanol (diisopropyl carbinol), 2,2,4-trimethyl-3-pentanol, and 2,2,4-trimethyl-1-pentanol was found in the final reaction mixture.

Comparative Example 4

Isomerization in the Absence of Hydrogen

The same catalyst in Example 1 (2 g) was loaded in a 100 mL stainless steel autoclave reactor with 6 g of trans-2,2,4,4-tetramethylcyclobutane-1,3-diol and 54 g of isobutyl isobutyrate. The autoclave was agitated and purged twice with helium 0.7 MPa (100 psig) at ambient temperature and then heated to 150° C. After 4 hours, a product sample was taken and analyzed by GC. The conversion of trans-2,2,4,4-tetramethylcyclobutane-1,3-diol was 2.6% and the ratio of cis to trans isomers was 0.027:1.

Comparative Example 5

Isomerization with a supported Ni catalyst

Four grams of a Ni-3288 catalyst (purchased from BASF Catalysts) having a surface area of 160 $m^2/g$ and containing 39 weight percent NiO, 31 weight percent Ni, 13 weight percent Bentonite clay, 13 weight percent alumina, 3 weight percent calcium silicate, and 0.1-1 weight percent crystalline silica), were placed in a 100 mL stainless steel autoclave reactor with 72 g of isobutyl isobutyrate. The autoclave was agitated and purged twice with helium a pressure of 0.7 MPa (100 psig) and then with hydrogen at pressure of 0.7 MPa (100 psig) at ambient temperature. The autoclave was heated to 150° C., and the reactor pressure was increased to 2.8 MPa (400 psig) with hydrogen. After the 2 hours, the reactor was cooled approximately 50° C. Six grams of trans-2,2,4,4-tetramethylcyclobutane-1,3-diol were then added to the reactor. The autoclave was agitated and purged twice with helium a pressure of 0.7 MPa (100 psig) followed by hydrogen, also at a pressure of 0.7 MPa (100 psig). The autoclave was then heated to 150° C. and pressurized to 2.8 MPa (400 psig) with hydrogen. After 5 hours, a product sample was taken and analyzed by GC. The conversion of trans-2,2,4,4-tetramethylcyclobutane-1,3-diol was 1.2% and the ratio of cis to trans isomers was 0.22:1.

Example 6

The same catalyst in Example 1 (0.9 g) was loaded in a 100 mL stainless steel autoclave reactor with eight grams of cis-2,2,4,4-tetramethylcyclobutane-1,3-diol and 72 g of isobutyl isobutyrate. The autoclave was agitated and purged twice with helium a pressure of 0.7 MPa (100 psig) at ambient temperature and then purged with hydrogen a pressure of 0.7 MPa (100 psig). The autoclave was then heated to 120° C. and pressurized to 2.8 MPa (400 psig) with hydrogen. After 3 hours, a product sample was taken and analyzed by GC. The conversion of cis-2,2,4,4-tetramethylcyclobutane-1,3-diol was 25% and the ratio of cis to trans isomers was 2.93:1.

Example 7

A 300 mL stainless steel autoclave was charged with a mixture of 6 g 90% trans-2,2,4,4-tetramethylcyclobutane-1,3-diol, 144 g water and a catalyst basket loaded with 5 grams of 2 weight percent Ru on a-alumina catalyst (surface area=10 $m^2/g$, obtained from BASF Catalysts). The autoclave was agitated and purged three times with nitrogen at 0.7 MPa (100 psig) then with hydrogen at 1.4 MPa (200 psig) at ambient temperature. The autoclave was then heated to 120° C. and pressurized to 3.5 MPa (500 psig) with hydrogen. Samples were taken from the autoclave at 1, 3, 5, 10, 20, 30, 60, 90 and 120 minutes intervals and analyzed by gas chromatography (GC). After 30 minutes, the ratio of cis to trans isomers was 1.8:1, remaining essentially the same for the final samples. Conversion of the trans isomer was 64.5% to products. 2,2,4-Trimethyl-1,3-pentanediol (0.5% relative to the cis and trans diols) was the only byproduct detectable by GC analysis in the final sample.

Example 8

A 300 mL stainless steel autoclave was charged with a mixture of 6 g>98% cis-2,2,4,4-tetramethylcyclobutane-1,3- diol, 144 g water and a catalyst basket loaded with 5 grams of 2 weight percent Ru on α-alumina catalyst (surface area=10 m²/g, obtained from BASF Catalysts). The autoclave was agitated and purged three times with nitrogen at 0.7 MPa (100 psig) then with hydrogen at 1.4 MPa (200 psig) at ambient temperature. The autoclave was then heated to 120° C. and pressurized to 3.5 MPa (500 psig) with hydrogen. Samples were taken from the autoclave at 1, 3, 5, 10, 20, 30, 60, 90 and 120 minutes intervals and analyzed by gas chromatography (GC). After 60 minutes, the ratio of cis to trans isomers was 1.8:1 (65% and 35% respectively, by GC analysis), remaining essentially the same for the final samples. No byproduct was detectable by GC analysis in the final sample.

We claim:

1. A process for the isomerization of a 2,2,4,4-tetraalkyl-cyclobutane-1,3-diol, comprising contacting a starting 2,2,4,4-tetraalkylcyclobutane-1,3-diol having a molar ratio of cis to trans isomers of about 0:1 to about 1.5:1 with hydrogen in the presence of a catalyst comprising about 0.1 to about 10 weight percent ruthenium, based on the total weight of the catalyst, deposited on a support, to produce an isomerized 2,2,4,4-tetraalkylcyclobutane-1,3-diol having a different molar ratio of cis to trans isomers than the starting 2,2,4,4-tetraalkylcyclobutane-1,3-diol, wherein the process has no net production of 2,2,4,4-tetraalkylcyclobutane-1,3-diol.

2. The process according to claim 1 wherein the starting 2,2,4,4-tetraalkylcyclobutane-1,3-diol has the general formula:

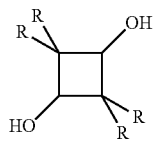

wherein R is methyl, ethyl, propyl, isopropyl, butyl, isobutyl, pentyl, hexyl, heptyl, or octyl; and the support comprises silica, alumina, silica-alumina, titania, zirconia, activated carbon, graphite, graphitized carbon, carbon nanotubes, zeolites, chromia, rare earth metal oxides, or mixtures thereof.

3. The process according to claim 2 wherein R is methyl.

4. The process according to claim 3 wherein the starting 2,2,4,4-tetraalkylcyclobutane-1,3-diol has a cis:trans molar ratio of about 0:1 to less than 1:1 and the isomerized 2,2,4,4-tetraalkylcyclobutane-1,3-diol has a cis:trans molar ratio of greater than 1:1 to about 2:1.

5. The process according to claim 3 wherein the catalyst comprises about 1 to about 9 weight percent ruthenium and the support comprises activated carbon, carbon nanotubes, graphitized carbon, silica, alumina, or a mixture thereof.

6. The process according to claim 5 which is at a temperature of about 100 to about 200° C. and a hydrogen pressure of about 0.4 to about 2.8 megapascals.

7. The process according to claim 6 wherein the starting 2,2,4,4-tetraalkylcyclobutane-1,3-diol is dissolved in at least one solvent selected from water, alcohols, ethers, glycols, glycol ethers, alkanes, and esters.

8. The process according to claim 7 wherein the solvent is selected from water, methanol, ethanol, propanol, 1-butanol, 2-butanol, 2-ethylhexanol, 2,2-dimethyl-1,3-propanediol, ethylene glycol, propylene glycol, 1,4-butanediol, diethylene glycol, hexane, heptane, cyclohexane, octane, decane, diethyl ether, diisopropyl ether, tetrahydrofuran, methyl tert-butyl ether, ethylene glycol monobutyl ether, diethylene glycol monobutyl ether, ethyl acetate, n-propyl acetate, isopropyl isobutyrate, isobutyl propionate, octyl acetate, isobutyl isobutyrate, isobutyl acetate, methyl butyrate, and mixtures thereof.

9. The process according to claim 1 which is a continuous process.

10. The process according to claim 1 wherein the process is conducted in the liquid phase, vapor phase, or a combination of liquid and vapor phase.

11. The process according to claim 3 wherein the starting 2,2,4,4-tetraalkylcyclobutane-1,3-diol is produced by hydrogenation of 2,2,4,4-tetramethylcyclobutane-1,3-dione.

12. A process for the isomerization of a 2,2,4,4-tetraalkylcyclobutane-1,3-diol, comprising contacting trans-2,2,4,4-tetramethylcyclobutane-1,3-diol with a catalyst comprising about 1 to about 9 weight percent ruthenium, based on the total weight of the catalyst, deposited on a support comprising silica, alumina, silica-alumina, titania, zirconia, activated carbon, carbon nanotubes, graphitized carbon, zeolites, chromia, rare earth metal oxides, or mixtures thereof at a pressure of about 0.4 to about 3.5 megapascals and a temperature of about 100 to about 250° C. to form cis-2,2,4,4-tetramethylcyclobutane-1,3-diol, wherein the process has no net production of 2,2,4,4-tetraalkylcyclobutane-1,3-diol.

13. The process according to claim 12 wherein the trans-2,2,4,4-tetramethylcyclobutane-1,3-diol is dissolved in at least one solvent selected from water, alcohols, ethers, glycols, glycol ethers, alkanes, and esters.

14. The process according to claim 13 wherein the solvent is selected from water, methanol, ethanol, propanol, 1-butanol, 2-butanol, 2-ethylhexanol, 2,2-dimethyl-1,3-propanediol, ethylene glycol, propylene glycol, 1,4-butanediol, diethylene glycol, hexane, heptane, cyclohexane, octane, decane, diethyl ether, diisopropyl ether, tetrahydrofuran, methyl tert-butyl ether, ethylene glycol monobutyl ether, diethylene glycol monobutyl ether, ethyl acetate, n-propyl acetate, isopropyl isobutyrate, isobutyl propionate, octyl acetate, isobutyl isobutyrate, methyl butyrate, isobutyl acetate, and mixtures thereof.

15. The process according to claim 14 wherein the support comprises alumina, activated carbon, graphitized carbon, silica, silica-alumina, or carbon nanotubes.

16. A process for the isomerization of a 2,2,4,4-tetraalkylcyclobutane-1,3-diol, comprising contacting a starting 2,2,4,4-tetraalkylcyclobutane-1,3-diol having a molar ratio of cis to trans isomers of 3:1 to about 20:1 with hydrogen in the presence of a catalyst comprising about 0.1 to about 10 weight percent ruthenium, based on the total weight of the catalyst, deposited on a support, to produce an isomerized 2,2,4,4-tetraalkylcyclobutane-1,3-diol having a molar ratio of cis to trans isomers of about 1.5:1 to about 5:1, wherein the process has no net production of 2,2,4,4-tetraalkylcyclobutane-1,3-diol.

17. The process according to claim 16 which is a continuous process.

18. The process according to claim 16 wherein the starting 2,2,4,4-tetramethylcyclobutane-1,3-diol is dissolved in a solution comprising water, methanol, ethanol, propanol, 1-butanol, 2-butanol, 2-ethylhexanol, 2,2-dimethyl-1,3-propanediol, ethylene glycol, propylene glycol, 1,4-butanediol, diethylene glycol, hexane, heptane, cyclohexane, octane, decane, diethyl ether, diisopropyl ether, tetrahydrofuran, methyl tert-butyl ether, ethylene glycol monobutyl ether, diethylene glycol monobutyl ether, ethyl acetate, n-propyl acetate, isopropyl isobutyrate, isobutyl propionate, octyl acetate, isobutyl isobutyrate, isobutyl acetate methyl butyrate, or mixtures thereof at a concentration of about 10 to about 25 weight percent, based on the total weight of the solution.

* * * * *